United States Patent
Okuma

(10) Patent No.: US 8,959,878 B2
(45) Date of Patent: Feb. 24, 2015

(54) TABLET INSPECTING DEVICE

(75) Inventor: Keiji Okuma, Kumamoto (JP)

(73) Assignee: Ookuma Electronic Co., Ltd., Kumamoto-shi (JP)

( * ) Notice: Subject to any disclaimer, the term of this patent is extended or adjusted under 35 U.S.C. 154(b) by 772 days.

(21) Appl. No.: 13/275,933

(22) Filed: Oct. 18, 2011

(65) Prior Publication Data

US 2012/0096807 A1   Apr. 26, 2012

(30) Foreign Application Priority Data

Oct. 20, 2010 (JP) ................ 2010-235378

(51) Int. Cl.
| | | |
|---|---|---|
| B65B 57/10 | (2006.01) | |
| B65B 9/08 | (2012.01) | |
| A61J 1/10 | (2006.01) | |
| A61J 3/00 | (2006.01) | |
| G01N 21/95 | (2006.01) | |
| B65B 65/08 | (2006.01) | |

(52) U.S. Cl.
CPC ... B65B 9/08 (2013.01); A61J 1/10 (2013.01); A61J 3/00 (2013.01); B65B 65/08 (2013.01); G01N 21/9508 (2013.01)
USPC .................. 53/500; 382/143; 53/550; 53/393; 53/167; 198/339.1

(58) Field of Classification Search
CPC ............ B65B 9/08; B65B 1/30; B65B 57/10; B65B 65/08; B65B 57/20; B65B 57/00; A61J 1/10; A61J 3/00; G01N 21/88
USPC .......... 53/507, 508, 500, 550, 562, 167, 393; 198/861.2, 861.3, 837, 842, 836.1, 198/836.4; 382/143
See application file for complete search history.

(56) References Cited

U.S. PATENT DOCUMENTS

| | | | | |
|---|---|---|---|---|
| 6,205,237 | B1 * | 3/2001 | Focke et al. | 382/141 |
| 6,505,461 | B1 * | 1/2003 | Yasunaga | 53/562 |
| 6,661,868 | B2 * | 12/2003 | Sawada | 378/57 |
| 7,792,349 | B2 * | 9/2010 | Van Den Brink | 382/141 |

(Continued)

FOREIGN PATENT DOCUMENTS

| | | |
|---|---|---|
| JP | 2004-236997 | 8/2004 |
| JP | 2004-238066 | 8/2004 |

(Continued)

*Primary Examiner* — Stephen F Gerrity
*Assistant Examiner* — Eyamindae Jallow
(74) *Attorney, Agent, or Firm* — Jordan and Hamburg LLP

(57) ABSTRACT

A tablet inspecting device which can overcome counting and discrimination errors is provided. A medicine packaging envelope strip is formed by connecting in a strip shape multiple envelopes separated when a user takes tablets, and is imaged, thus counting the tablets. A conveyance passage along which the strip is conveyed in an associated longitudinal direction, conveyance mechanism, and gap forming part forming a gap between adjacent tablets, the conveyance passage including a horizontal passage, a first inclined passage with upward inclination extending from the horizontal passage, and a second inclined passage with downward inclination and an upper end spaced apart from an upper end of the first passage, the gap forming part including a rod body having projecting portions staggered throughout a peripheral surface thereof, being arranged at the space approximately orthogonal to the conveyance direction, and being rotatable about a center axis thereof, are provided.

8 Claims, 12 Drawing Sheets

(56) References Cited

U.S. PATENT DOCUMENTS

| | | | |
|---|---|---|---|
| 7,796,799 B2 * | 9/2010 | Jorritsma | 382/141 |
| 8,085,395 B2 * | 12/2011 | Jorritsma | 356/240.1 |
| 2004/0089522 A1 * | 5/2004 | Shaum | 198/861.1 |
| 2004/0250514 A1 * | 12/2004 | Brenkus | 53/415 |
| 2009/0038455 A1 * | 2/2009 | Strong et al. | 83/155.1 |
| 2013/0299381 A9 * | 11/2013 | Luciano, Jr. | 206/534 |

FOREIGN PATENT DOCUMENTS

| | | |
|---|---|---|
| JP | 2004-269008 | 9/2004 |
| JP | 4225534 | 12/2008 |

* cited by examiner

TABLET INSPECTING DEVICE

FIELD OF THE INVENTION

The present invention relates to a tablet inspecting device where a medicine packaging envelope in which tablets are sealed is imaged thus automatically inspecting the tablets in the medicine packaging envelope, and more particularly to a technique which arranges the tablets in a neatly accommodated state in preparation for imaging.

DESCRIPTION OF THE RELATED ART

Conventionally, in a dispensary of a hospital, a pharmacy or the like, one-pouch packaging (or one dose packaging) is adopted. In one one-pouch packaging, medicines consisting of plural kinds of tablets or the like to be dosed by a patient at a time are offered in a state where the medicines are sealed in each medicine packaging envelope using a known automatic dispensing device, for example. Here, to count the number of medicines sealed in the medicine packaging envelope or to check kinds of medicines in the medicine packaging envelope and to exclude the medicine packaging envelope where the number of sealed medicines is found abnormal or the kind of medicine is found abnormal are extremely important from a viewpoint of offering medicines which conform to the prescription to a patient.

Accordingly, for example, there has been proposed a medicine counting device which counts the number of tablets in a medicine packaging envelope by imaging a silhouette image of the medicine packaging envelope and by automatically counting the number of silhouettes of the tablets appearing in the image. Further, there has been also proposed a tablet inspecting device such as a medicine indentifying device which identifies kinds of tablets based on reflection images from the tablets accommodated in a medicine packaging envelope, for example.

However, depending on a medicine accommodating state in the medicine packaging envelope, there may be a case where the tablets overlap with each other or are brought into contact with each other. In such a case, there exists a possibility that the number of the above-mentioned silhouette and the number of actual tablets differ from each other thus causing a counting error. Further, there also exists a possibility that the identification of tablets one by one from the above-mentioned reflection images becomes difficult.

In view of such circumstances, various proposals have been made to overcome such drawbacks (see Japanese Patent 4225534 (patent document 1), for example).

SUMMARY OF THE INVENTION

Patent document 1 discloses a tablet counting and inspecting device which images an envelope such as a medicine packaging envelope and automatically confirms the number of tablets in the envelope. The tablet counting and inspecting device includes a clamping mechanism which temporarily presses an edge portion of the envelope, a vibrating mechanism which vibrates the envelope pressed by the clamping mechanism, and a loosening imparting mechanism which loosens the envelope at a position where the envelope is pressed by the clamping mechanism.

However, according to patent document 1, the tablet counting and inspecting device is configured to widen a gap between the adjacent tablets by making use of vibrations applied to the tablets by the vibrating mechanism. Accordingly, for example, when both tablets move while keeping a contact state during the vibrations, it is not always guaranteed that the vibrations act in the direction that the contact between the tablets is separated. Accordingly, patent document 1 has a possibility that the tablets are imaged in a state where the tablets are arranged adjacent to each other thus giving rise to a drawback that the error in counting the number of tablets or the difficulty in discriminating the tablets has not been overcome yet.

The present invention has been made in view of such drawbacks, and it is an object of the present invention to provide a tablet inspecting device which can accurately inspect tablets by overcoming an error in counting the number of tablets or the difficulty in discriminating the tablets which occurs when tablets which are accommodated in a medicine packaging envelope are arranged adjacent to each other.

According to one aspect of the present invention, there is provided a tablet inspecting device in which a medicine packaging envelope strip which is formed in a strip shape by continuously connecting a plurality of medicine packaging envelopes each of which accommodates tablets in the inside thereof and is separated when a user takes the tablets is imaged thus inspecting the tablets in the inside of the medicine packaging envelope, the tablet inspecting device which includes: a conveyance passage along which the medicine packaging envelope strip placed thereon is conveyed in the longitudinal direction of the medicine packaging envelope strip; a conveyance mechanism which conveys the medicine packaging envelope strip along the conveyance passage; and a gap forming part which forms a gap between the adjacent tablets, wherein the conveyance passage includes: a horizontal conveyance passage along which the medicine packaging envelope strip is conveyed in an approximately horizontal state; a first inclined passage with upward inclination which extends from the horizontal conveyance passage in the conveyance direction; and a second inclined passage with downward inclination having an upper end at a position slightly spaced apart from an upper end of the first inclined passage in the conveyance direction, wherein the gap forming part includes a rod body which is provided with a plurality of projecting portions arranged in a staggered manner at predetermined intervals on a peripheral surface thereof, is arranged at the space formed between the upper ends in a state approximately orthogonal to the conveyance direction, and is rotatable about a center axis thereof, and the medicine packaging envelope strip is conveyed over the rod body while rotating the rod body thus forming a gap between the tablets by way of the projecting portion.

In the tablet inspecting device having the above-mentioned constitution, the tablet inspecting device includes a flipping mechanism which flips one side portion of the medicine packaging envelope strip conveyed along the horizontal conveyance passage so as to scatter the tablets accommodated in a state where the tablets are densely collected on a side portion side within the medicine packaging envelope.

In the tablet inspecting device having the above-mentioned constitution, the flipping mechanism includes: an elongated resilient member which extends downward on the side of the horizontal conveyance passage, wherein an upper end side of the elongated resilient member is supported and a lower end side of the elongated resilient member forms a free end at a position slightly away from the side of the horizontal conveyance passage; and a hammer portion which is rotated below the elongated resilient member and intermittently resiliently deforms a lower end side of the elongated resilient member in the direction approximately orthogonal to the conveyance direction and away from the medicine packaging envelope strip, wherein the elongated resilient member flips the side portion of the medicine packaging envelope strip when the elongated resilient member returns to an original state from an elastically deformed state.

In the tablet inspecting device having the above-mentioned constitution, the tablet inspecting device further includes an overlapping releasing part which includes a columnar or cylindrical rotary body which is arranged above the horizontal conveyance passage in a state where a center axis of the rotary body is approximately orthogonal to the conveyance direction and is rotatable about the center axis thereof, the overlapping releasing part being capable of releasing overlapping of the tablets which are accommodated in the medicine packaging envelope strip in a vertically overlapped state when the medicine packaging envelope strip passes a gap defined between the horizontal conveyance passage and the rotary body.

In the tablet inspecting device having the above-mentioned constitution, the gap forming part includes a biasing mechanism which constantly biases the rod body upward.

In the tablet inspecting device having the above-mentioned constitution, the gap forming part includes an elevating/lowering mechanism which elevates and lowers the rod body.

In the tablet inspecting device having the above-mentioned constitution, a guide plate having an approximately inverse-V-shape which guides a distal end of the medicine packaging envelope strip is provided at the space.

In the tablet inspecting device having the above-mentioned constitution, the rotary body is elevatably provided.

According to the present invention, in the tablet inspecting device in which the medicine packaging envelope strip which is formed in a strip shape by continuously connecting the plurality of medicine packaging envelopes each of which accommodates tablets in the inside thereof and is separated when a user takes the tablets is imaged thus inspecting the tablets in the inside of the medicine packaging envelope, the tablet inspecting device includes: the conveyance passage along which the medicine packaging envelope strip placed thereon is conveyed in the longitudinal direction of the medicine packaging envelope strip; the conveyance mechanism which conveys the medicine packaging envelope strip along the conveyance passage; and the gap forming part which forms the gap between the adjacent tablets, wherein the conveyance passage includes: the horizontal conveyance passage along which the medicine packaging envelope strip is conveyed in an approximately horizontal state; the first inclined passage with upward inclination which extends from the horizontal conveyance passage in the conveyance direction; and the second inclined passage with downward inclination having an upper end at a position slightly spaced apart from an upper end of the first inclined passage in the conveyance direction, wherein the gap forming part includes the rod body which is provided with the plurality of projecting portions arranged in a staggered manner at predetermined intervals on the peripheral surface thereof, is arranged at the space formed between the upper ends in the state approximately orthogonal to the conveyance direction, and is rotatable about a center axis thereof, and the medicine packaging envelope strip is conveyed over the rod body while rotating the rod body thus forming a gap between the tablets by way of the projecting portion.

Due to such a constitution, in conveying the medicine packaging envelope strip while rotating the rod body, the adjacent tablets in a contact state are separated from each other in such a manner that one tablet is caught by each lattice formed by the projecting portions arranged in a staggered manner and hence, a gap can be formed between the adjacent tablets whereby it is possible to overcome an error in counting tablets or the difficulty in discriminating tablets which are caused due to the close contact of the tablets accommodated in the medicine packaging envelope thus providing a tablet inspecting device which can accurately inspect the tablets.

Further, according to the present invention, the tablet inspecting device includes the flipping mechanism which flips one side portion of the medicine packaging envelope strip conveyed along the horizontal conveyance passage so as to scatter the tablets accommodated in a state where the tablets are densely collected on the side portion side within the medicine packaging envelope.

Due to such a constitution, even when the tablets are sealed in the medicine packaging envelope in a state where the tablets are densely collected on one side of the medicine packaging envelope strip in the lateral direction, these tablets can be scattered in the inside of the medicine packaging envelope by flipping the side portion side of the medicine packaging envelope by the flipping mechanism and hence, a gap can be formed between the tablets more reliably by the gap forming part whereby it is possible to provide a tablet inspecting device which exhibits higher inspection accuracy and is highly practicable.

Further, according to the present invention, the flipping mechanism includes: the elongated resilient member which extends downward on the side of the horizontal conveyance passage, wherein the upper end side of the elongated resilient member is supported and the lower end side of the elongated resilient member forms the free end at a position slightly away from the side of the horizontal conveyance passage; and the hammer portion which is rotated below the elongated resilient member and intermittently resiliently deforms the lower end side of the elongated resilient member in the direction approximately orthogonal to the conveyance direction and away from the medicine packaging envelope strip, wherein the elongated resilient member flips the side portion of the medicine packaging envelope strip when the elongated resilient member returns to an original state from an elastically deformed state.

Due to such a constitution, even when the tablets are sealed in the medicine packaging envelope in a state where the tablets are densely collected on one side of the medicine packaging envelope strip in the lateral direction, it is possible to realize a tablet inspecting device which can inspect tablets with high accuracy with the simple mechanism thus suppressing the increase of a manufacturing cost and a maintenance cost.

Further, according to the present invention, the tablet inspecting device further includes the overlapping releasing part which includes the columnar or cylindrical rotary body which is arranged above the horizontal conveyance passage in a state where the center axis of the rotary body is approximately orthogonal to the conveyance direction and is rotatable about the center axis thereof, the overlapping releasing part being capable of releasing overlapping of the tablets which are accommodated in the medicine packaging envelope strip in a vertically overlapped state when the medicine packaging envelope strip passes the gap defined between the horizontal conveyance passage and the rotary body.

Due to such a constitution, by setting a size of a gap formed between the horizontal conveyance passage and the rotary body to a thickness of an approximately one tablet, even when the tablets are accommodated in a state where the tablets overlap with each other vertically, the tablets can be conveyed to the gap forming part in a state where the overlapping of the tablets is released by the overlapping releasing part whereby it is possible to provide a tablet inspecting device which can easily form the gap thus exhibiting higher inspection accuracy.

Further, according to the present invention, the gap forming part includes the biasing mechanism which always biases the rod body upward.

Due to such a constitution, by vertically moving the rod body corresponding to a weight of the medicine, the shape of the bottom surface of the medicine packaging envelope or the like, it is possible to prevent breaking of the medicine packaging envelope, the deformation or flaws of the tablets or the like due to applying of an excessively large force from the projecting portion to a bottom surface of the medicine packaging envelope when the rod body is rotated.

Further, according to the present invention, the gap forming part includes the elevating/lowering mechanism which elevates and lowers the rod body.

Due to such a constitution, a height of the rod body can be adjusted when necessary in such a manner that when a distal end of the medicine packaging envelope strip passes the space, the rod body is lowered so as to prevent the rod body from interfering the passing, while when the rod body is elevated to a height where the rod body is brought into contact with the medicine packaging envelope strip after passing. Accordingly, it is possible to provide a tablet inspecting device which can smoothly perform a conveyance of the medicine packaging envelope strip and is highly practicable.

Further, according to the present invention, the guide plate having an approximately inverse-V-shape which guides the distal end of the medicine packaging envelope strip is provided at the space.

Due to such a constitution, even when the distal end of the medicine packaging envelope strip is conveyed to the space in a state where the distal end of the medicine packaging envelope strip floats from the conveyance passage, the distal end can be smoothly guided to the second inclined passage by the guide plate whereby it is possible to provide the tablet inspecting device which can smoothly convey the medicine packaging envelope strip and is highly practicable.

Further, according to the present invention, the rotary body is elevatably provided.

Due to such a constitution, for example, the gap between the horizontal conveyance passage and the rotary body can be displaced in a desired manner corresponding to a size, posture or the like of the accommodated tablet and hence, it is possible to provide a tablet inspecting device which can surely release overlapping of the tablets in the vertical direction corresponding to the size, the posture or the like of the accommodated tablet.

DESCRIPTION OF THE PREFERRED EMBODIMENTS

Hereinafter, a tablet inspecting device according to an embodiment of the present invention is explained in conjunction with drawings.

In the explanation made hereinafter, tablets means not only tablets which are formed by compressing effective ingredients or the like, but also capsules which are formed by filling medicines in a powdery form or medicines in a liquid form therein and the like.

Figure 1:
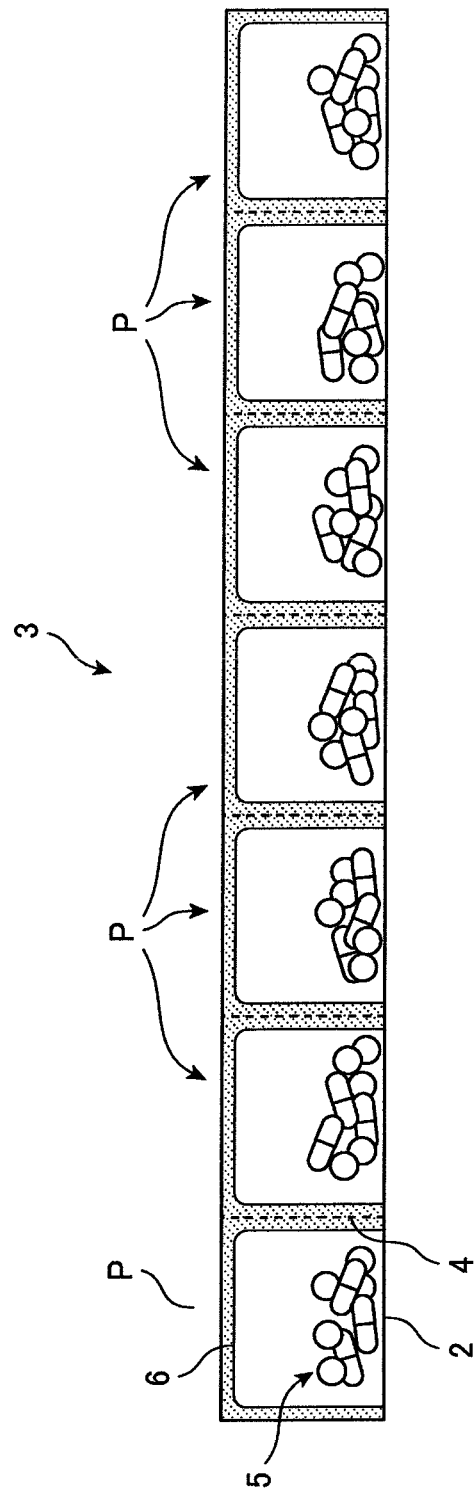
FIG. 1 is an explanatory plan view for explaining a medicine packaging envelope strip according to an embodiment of the present invention.

A medicine packaging envelope strip 3 according to this embodiment is a known medicine packaging envelope sheet body which is used for accommodating tablets or the like in a hospital, a pharmacy or the like. As shown in FIG. 1, the medicine packaging envelope strip 3 is a sheet body which is formed by continuously connecting a plurality of medicine packaging envelopes in each of which tablets are accommodated in a strip shape. In the medicine packaging envelope strip 3, medicine packaging envelopes P which are continuously connected in a strip shape can be formed, for example, by folding or doubling a strip-like sheet material along the longitudinal direction thus forming a folded side 2 (see FIG. 1), and upper and lower sheets are thermally welded to each other at predetermined intervals in the longitudinal direction. Further, as shown in FIG. 1, to separate these contiguously connected medicine packaging envelopes P respectively, perforated holes 4 for cutting are formed in thermally welded portions orthogonal to the longitudinal direction of the medicine packaging envelope strip 3.

In each medicine packaging envelope P formed in this manner, using a known tablet dispenser (not shown in the drawing), for example, tablets 5 are charged and accommodated in accordance with a prescription. In charging the tablets into each medicine packaging envelope P, a side 6 of the medicine packaging envelope P which is arranged opposite to the folded side 2 of the medicine packaging envelope P is opened in a non-welded state and, thereafter, the side 6 is also welded and closed after the tablets 5 are charged into the medicine packaging envelope P through the opened side 6. In this embodiment, a plurality of tablets 5 are charged into the medicine packaging envelope P in a state where the side 6 is directed upward and hence, there exists a tendency that these tablets 5 are accommodated in the medicine packaging envelope P in a non-uniform concentrated manner on the folded side 2 (see FIG. 1).

Figure 2:
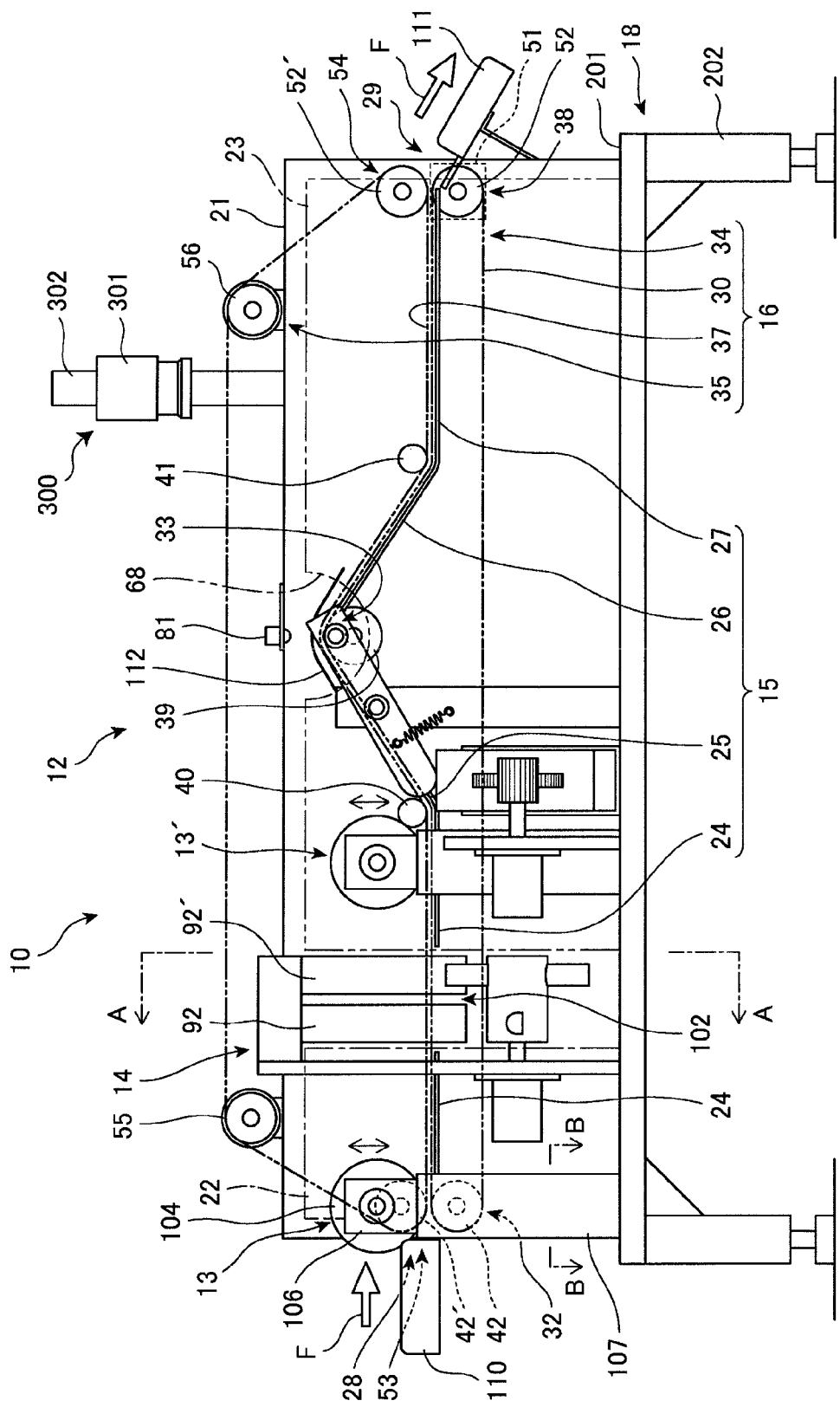
FIG. 2 is a schematic front view for explaining the whole constitution of a tablet inspecting device according to the embodiment of the present invention.
Figure 3:
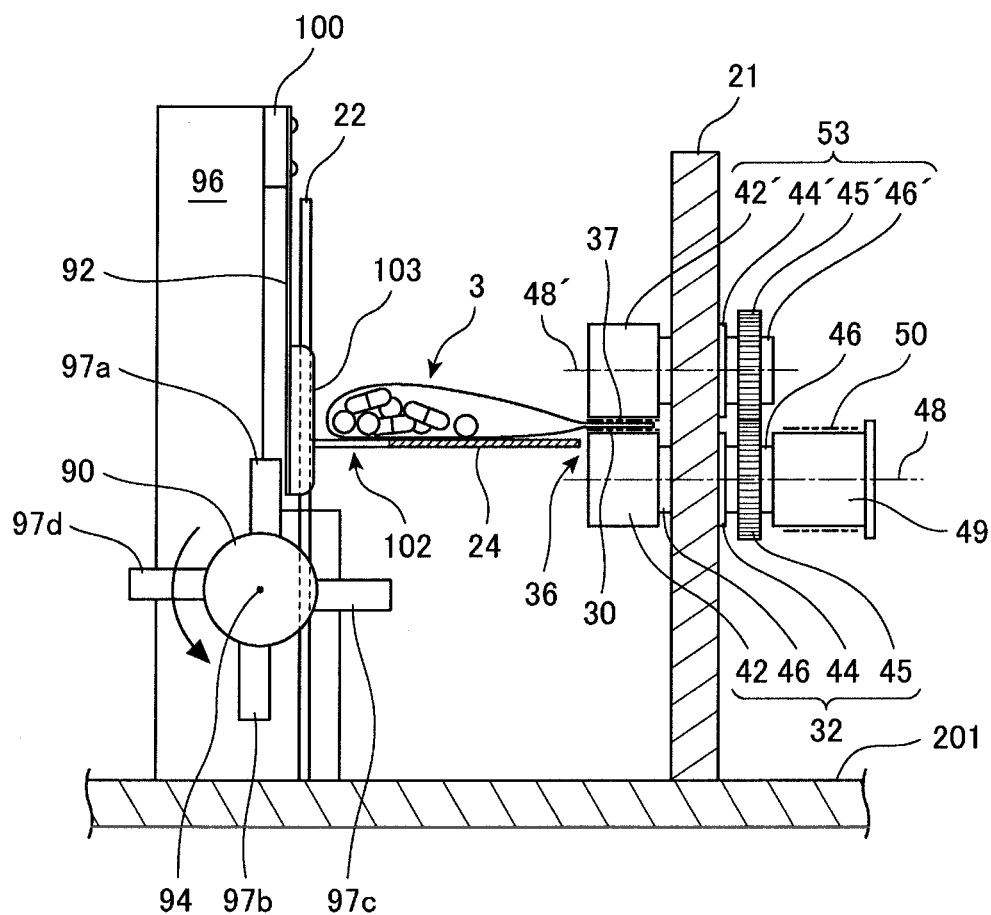
FIG. 3 is a cross-sectional view taken along a line A-A in FIG. 2 with a part broken away of the tablet inspecting device according to the embodiment of the present invention.

The schematic constitution of the tablet inspecting device 10 according to this embodiment of the present invention is explained mainly in conjunction with FIG. 2 and FIG. 3. The tablet inspecting device 10 of this embodiment includes a conveyance passage 15, a conveyance mechanism 16, a support portion 18 which supports the conveyance passage 15 and the conveyance mechanism 16, an inspecting part 300, a gap forming part 12 which constitutes an essential part of this embodiment, overlapping releasing parts 13, 13', and a flipping mechanism 14.

Firstly, the conveyance passage 15 of this embodiment is a passage along which the medicine packaging envelope strip 3 is conveyed in the longitudinal direction of the medicine packaging envelope strip 3 in a state where the medicine packaging envelope strip 3 is placed on the conveyance passage 15, and a space 33 is formed in a midst portion of the conveyance passage 15. As shown in FIG. 2, an entrance opening 28 of the tablet inspecting device 10 of this embodiment is formed one end side of the conveyance passage 15, and an exit opening 29 of the tablet inspecting device 10 is formed on the other end side of the conveyance passage 15. That is, the medicine packaging envelope strip 3 is conveyed into the inside of the tablet inspecting device 10 from the entrance opening 28 and is discharged from the exit opening 29 of the tablet inspecting device 10. In FIG. 2, symbol F indicates the conveyance direction of the medicine packaging envelope strip 3.

The conveyance mechanism 16 is a mechanism which conveys the medicine packaging envelope strip 3 along an upper surface of the conveyance passage 15 in the conveyance direction F. The conveyance mechanism 16, as describes later, conveys the medicine packaging envelope strip 3 along the upper surface of the conveyance passage 15 while clamping the side 6 of the medicine packaging envelope strip 3 by belts from above and below (see FIG. 3).

In the tablet inspecting device 10 of this embodiment, as shown in FIG. 2, in the direction toward the exit opening 29 from the entrance opening 28 of the conveyance passage 15, the overlapping releasing part 13, the flipping mechanism 14, the overlapping releasing part 13', the gap forming part 12 and the inspecting part 300 are arranged in this order.

Hereinafter, the constitutions of the respective parts are explained specifically.

Firstly, as shown in FIG. 2 and FIG. 3, the support portion 18 of this embodiment includes a support plate 201, and a first wall body 21, a second wall body 22 and a third wall body 23 which are mounted on the support plate 201 in an upright manner. The first wall body 21, the second wall body 22 and the third wall body 23 extend in the conveyance direction. In FIG. 2, to facilitate the understanding of the constitution of the tablet inspecting device 10, the second wall body 22 and the third wall body 23 are indicated by an imaginary line (double-dashed chain line).

The support plate 201 is formed of a flat base plate having a rectangular shape. As shown in FIG. 2, the support plate 201 is arranged with a plate surface thereof held in an approximately horizontal state, and is mounted on a floor by way of leg portions 202.

As shown in FIG. 2 and FIG. 3, the first wall body 21 is formed of, for example, an elongated flat plate member having a size of approximately 60 cm×20 cm and extending in the conveyance direction, and the first wall body 21 is mounted on the support plate 201 in an upright manner such that long sides of the first wall body 21 are arranged approximately horizontally. Further, as shown in FIG. 2, one end side of the first wall body 21 in the conveyance direction is arranged on an entrance opening 28 side, and the other end side of the first wall body 21 in the conveyance direction is arranged on an exit opening 29 side.

Further, as shown in FIG. 2 and FIG. 3, the second wall body 22 is formed of a flat plate member having a length of approximately one fifth to one seventh of a length of the first wall body 21 in the conveyance direction, for example. The second wall body 22 is, as shown in FIG. 2 and FIG. 3, arranged so as to face the first wall body 21 in an opposed manner on the entrance opening 28 side of the first wall body 21 while being spaced apart from the first wall body 21 with a distance slightly larger than a width of the medicine packaging envelope strip 3.

Figure 8:
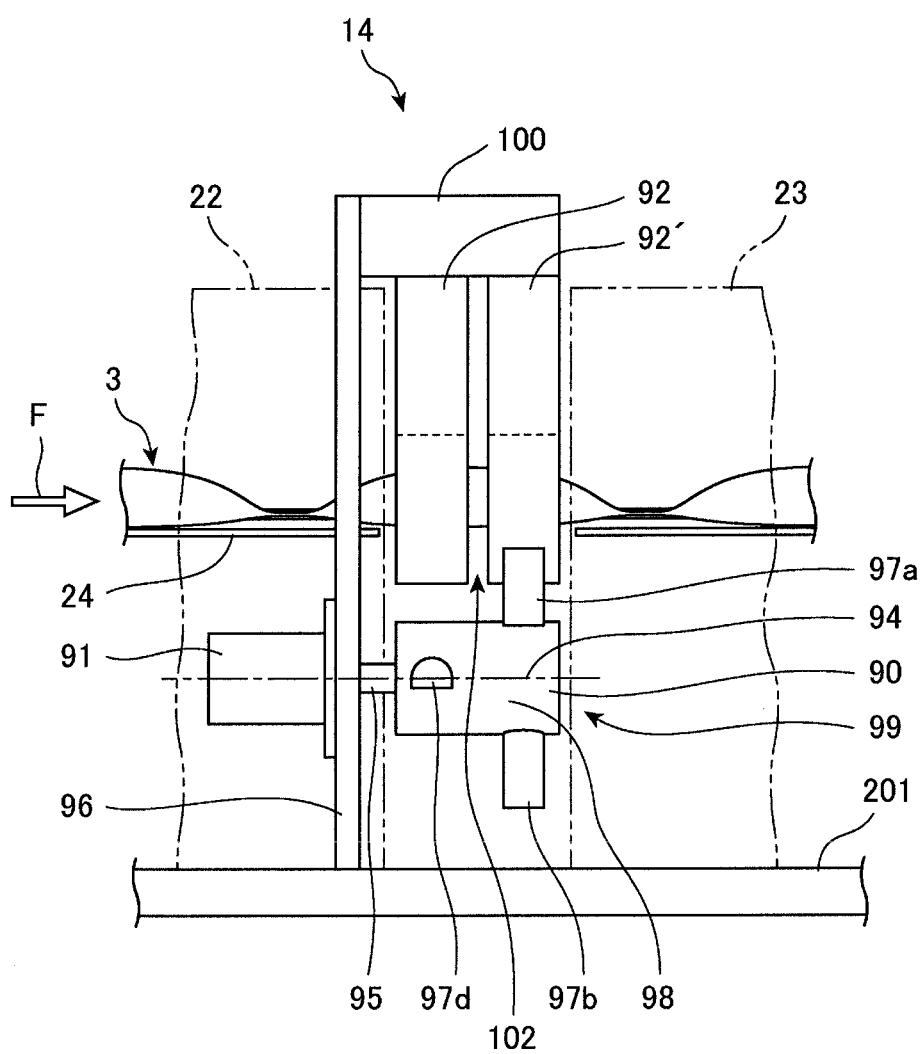
FIG. 8 is a front view for explaining a flipping mechanism of the tablet inspecting device according to the embodiment of the present invention.

Further, as shown in FIG. 2, the third wall body 23 is formed of a flat plate member having a length of approximately three fourth of a length of the first wall body 21 in the conveyance direction, for example. As shown in FIG. 2 and FIG. 8, the third wall body 23 is arranged so as to face the first wall body 21 in an opposed manner in a state where the third wall body 23 is spaced apart from an end of the second wall body 22 in the conveyance direction F by a distance 1 to 1.5 times as long as a length of the medicine packaging envelope P (see FIG. 4). That is, as shown in FIG. 2 and FIG. 3, the medicine packaging envelope strip 3 in a laid state can pass through a space defined between the first wall body 21 and the second wall body 22 as well as a space defined between the first wall body 21 and the third wall body 23 in the longitudinal direction of the medicine packaging envelope strip 3.

Here, to prevent the third wall body 23 from obstructing the movement of a rod body 60 described later, as shown in FIG. 2, a semispherical recessed portion 68 is formed on a portion of the third wall body 23 which faces a space 33 described later.

As shown in FIG. 2, the conveyance passage 15 of this embodiment includes a horizontal conveyance passage 24, a first inclined passage 25, a second inclined passage 26 and an inspection conveyance passage 27.

Firstly, as shown in FIG. 2 and FIG. 3, the horizontal conveyance passage 24 is formed of a rectangular flat plate member which has a width approximately equal to a width of the medicine packaging envelope strip 3 and a length sufficient for allowing placing of three to four medicine packaging envelopes P, for example, thereon. Further, as shown in FIG. 2 and FIG. 3, the horizontal conveyance passage 24 is arranged at a predetermined height between the first wall body 21 and the second wall body 22 with a plate surface thereof held in an approximately horizontal state, and one side edge of the horizontal conveyance passage 24 is fixed to inner surfaces of the second wall body 22 and the third wall body 23 respectively by welding. That is, the horizontal conveyance passage 24 of this embodiment is supported on the second wall body 22 and the third wall body 23 in a cantilever state (see FIG. 3). Further, as shown in FIG. 3, the horizontal conveyance passage 24 is arranged in a spaced apart manner in the widthwise direction from the first wall body 21 and hence, a roller 42 and the like which constitute the conveyance mechanism 16 described later are arranged in a space defined between the first wall body 21 and the horizontal conveyance passage 24.

In this manner, as shown in FIG. 2 and FIG. 11, the horizontal conveyance passage 24 can convey the medicine packaging envelope strip 3 in a state where the medicine packaging envelope strip 3 is placed on the horizontal conveyance passage 24 in a horizontal state.

In the tablet inspecting device 10 of this embodiment, as shown in FIG. 2, a guide passage 110 which guides the medicine packaging envelope strip 3 extends on an upstream side of the horizontal conveyance passage 24 in the conveyance direction.

Further, as shown in FIG. 2 and FIG. 3, a rectangular notch 102 is formed on a portion of the horizontal conveyance passage 24 corresponding to a space defined between the second wall body 22 and the third wall body 23. The notch 102 is provided for ensuring a movable range of leaf springs 92 which the flipping mechanism 14 described later includes (see FIG. 2 and FIG. 9), and the explanation of the notch 102 is made later again along with the explanation of the flipping mechanism 14.

Figure 4:
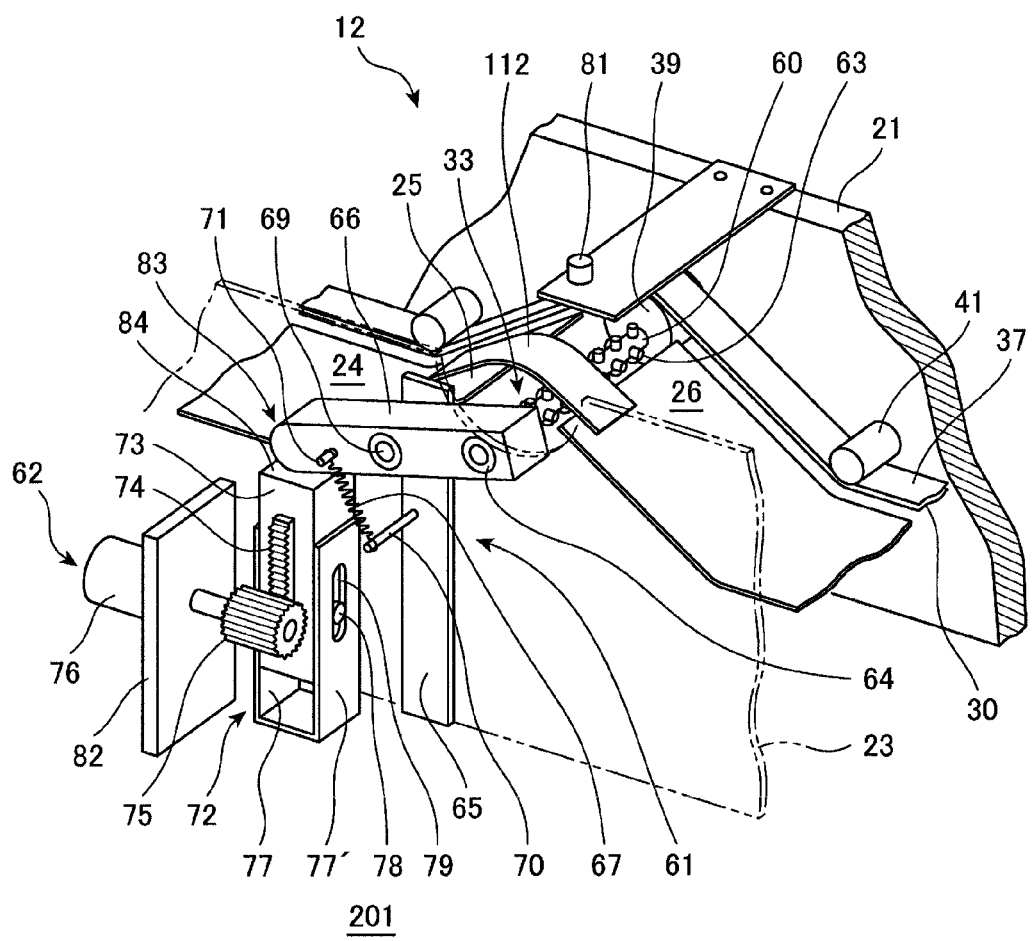
FIG. 4 is an explanatory perspective view for explaining a gap forming part of the tablet inspecting device according to the embodiment of the present invention.

As shown in FIG. 2, FIG. 4 and FIG. 5, the first inclined passage 25 is formed of a rectangular flat plate member which has a width approximately equal to a width of the medicine packaging envelope strip 3 and a length sufficient for allowing placing of approximately one to two medicine packaging envelopes P thereon, for example. As shown in FIG. 2 and FIG. 5, the first inclined passage 25 extends in the conveyance direction F from a downstream end of the horizontal conveyance passage 24 in an upwardly inclined manner at a predetermined inclination angle. It is desirable to set the predetermined inclination angle to approximately 30 degrees to 45 degrees with respect to the horizontal line. The reason is that when the predetermined inclination angle is large, there exists a possibility that tablets are densely collected on an upstream side of the medicine packaging envelope P due to weights of the tablets, and overlap with each other. The first inclined passage 25 which extends in this manner is, in the same manner as described above, supported on the third wall body 23 in a cantilever manner.

As shown in FIG. 2, FIG. 4 and FIG. 5, the second inclined passage 26 is formed of a rectangular flat plate member having a size substantially equal to a size of the first inclined passage 25, for example. Further, as shown in FIG. 4 to FIG. 6, the second inclined passage 26 is arranged in a downwardly inclined manner in the conveyance direction F at the approximately same angle as the first inclined passage 25 such that the second inclined passage 26 extends from a position which is spaced apart from an upper end of the first inclined passage 25 in the conveyance direction F by a distance approximately one tenth to one fifth of a length of folded side 2 of the medicine packaging envelope P, for example. In FIG. 2, FIG. 4, FIG. 5 and FIG. 6, numeral 33 indicates a space defined between the upper end of the first inclined passage 25 and an upper end of the second inclined passage 26. The second inclined passage 26 which is arranged in this manner is, in the same manner as the horizontal conveyance passage 34 and the first inclined passage 25 described above, supported on the third wall body 23 in a cantilever state.

In other words, as shown in FIG. 2, FIG. 5 and FIG. 6, the first inclined passage 25 and the second inclined passage 26 form equal sides of an approximately isosceles triangle which uses the space 33 as a vertex as viewed in a front view.

The inspection conveyance passage 27 is formed of a flat plate member having a size approximately equal to a size of the horizontal conveyance passage 24, for example. As shown in FIG. 2, the inspection conveyance passage 27 extends from a downstream end of the second inclined passage 26 approximately horizontally in the conveyance direction F, and is supported on the third wall body 23 in a cantilever state. That is, in this embodiment, the horizontal conveyance passage 24 and the inspection conveyance passage 27 are arranged at an approximately same height.

A downstream end side of the inspection conveyance passage 27 corresponds to the exit opening 29 described above.

The inspection conveyance passage 27 includes a rectangular opening (not shown in the drawing) having a size corresponding to approximately one medicine packaging envelope P for allowing a transmission light described later to pass therethrough.

In the tablet inspecting device 10 of this embodiment, a discharge passage 111 which discharges the medicine packaging envelope strip 3 also extends on a downstream side of the inspection conveyance passage 27.

The first inclined passage 25, the second inclined passage 26 and the inspection conveyance passage 27 are, in the same manner as the horizontal conveyance passage 24, arranged in a spaced apart manner from the first wall body 21 in the widthwise direction respectively. That is, the conveyance passage 15 of this embodiment is formed such that a strip-shaped space 36 having the substantially same width in the conveyance direction is formed between the first wall body 21 and the conveyance passage 15 over the whole length of the conveyance passage 15 (see FIG. 3). Further, rollers, endless belts and the like which constitute the conveyance mechanism 16 described later are arranged in the strip-shaped space 36.

As shown in FIG. 2 and FIG. 3, the conveyance mechanism 16 of this embodiment includes a first endless belt 30 which is arranged in the above-mentioned strip-shaped space 36, a second endless belt 37 which is arranged above the first endless belt 30, a first circulation mechanism 34 which makes the first endless belt 30 circulate approximately along an edge of the conveyance passage 15, and a second circulation mechanism 35 which makes the second endless belt 37 circulate approximately along a side edge of the conveyance passage 15.

The first circulation mechanism 34 of this embodiment includes, as shown in FIG. 2, an entrance side rotary part 32, an exit side rotary part 38, a first guide roller 39, a second guide roller 40, and a third guide roller 41.

As shown in FIG. 2 and FIG. 3, the entrance side rotary part 32 of this embodiment includes an entrance side roller 42, a shaft body 46, a bearing 44, and a main gear 45.

The entrance side roller 42 is, as shown in FIG. 2 and FIG. 3, formed of a columnar body which has a diameter substantially one third of the width of the medicine packaging envelope strip 3 and a width slightly smaller than the diameter thereof, for example. Further, as shown in FIG. 2 and FIG. 3, the entrance side roller 42 is arranged in the strip-shaped space 36 in the vicinity of the entrance opening 28 in a state where a center axis 48 of the columnar body orthogonally intersects with the conveyance direction F, and an upper end of the entrance side roller 42 is arranged at a height substantially equal to or slightly higher than the horizontal conveyance passage 24.

The shaft body 46 is, as shown in FIG. 3, formed of a columnar body which has a length substantially twice or three times as large as the width of the entrance side roller 42 and a diameter slightly smaller than the diameter of the entrance side roller 42, for example. As shown in FIG. 3, the shaft body 46 is arranged on one side surface of the entrance side roller 42 in a projecting manner in a state where the center axis 48 of the entrance side roller 42 passes the approximately center of the shaft body 46, and the shaft body 46 penetrates the first wall body 21.

The bearing 44 is formed of a known bearing, for example. The bearing 44 is, as shown in FIG. 3, mounted on the first wall body 21, and pivotally supports the shaft body 46 in a rotatable manner. In this manner, the entrance side roller 42 is configured to be rotatable about the center axis 48 within a vertical plane which is parallel to the conveyance direction F.

The main gear 45 is, as shown in FIG. 3, formed of a gear having a diameter larger than the diameter of the shaft body 46, is mounted on an intermediate portion of the shaft body 46 positioned immediately outside the bearing 44, and is rotated together with the shaft body 46 about the center axis 48. The main gear 45 is meshed with a driven gear 45' described later thus rotating the driven gear 45' so that an entrance side driven roller 42' of an entrance side driven rotary part 53 is rotated. This structure is described in detail later.

As shown in FIG. 3, the entrance side rotary part 32 of this embodiment includes a columnar pulley 49 which is contiguously connected to the shaft body 46, and is rotated together with the shaft body 46 so as to assist the rotation of the entrance side rotary part 32. The pulley 49 is described in detail later.

The exit side rotary part 38 of this embodiment includes a drive motor 51 in addition to constitutional elements substantially equal to the constitutional elements of the above-mentioned entrance side rotary part 32. That is, as shown in FIG. 2, the exit side rotary part 38 includes an exit side roller 52 which is formed of constitutional elements substantially equal to the constitutional elements of the entrance side roller 42, and also includes a shaft body (shaft body 46), a bearing (bearing 44) and a main gear (main gear 45). Further, the exit side roller 52 is configured to be rotatable about the center axis thereof within a vertical plane which is parallel to the conveyance direction F, and is arranged in the strip-shaped space 36 in the vicinity of the exit opening 29 in a state where an upper side of an outer peripheral surface of the exit side roller 52 is arranged at a height substantially equal to or slightly higher than the inspection conveyance passage 27.

The drive motor 51 is formed of an electric motor such as a known stepping motor. The drive motor 51 is contiguously connected to the shaft body (not shown in the drawing) of the exit side roller 52, and rotates the shaft body. Although a pulley (not shown in the drawing) which is formed of a constitutional element substantially equal to the constitutional element for forming the above-mentioned pulley 49 is mounted on the exit side rotary part 38, the pulley is integrally rotated with the shaft body by the drive motor 51 and hence, the pulley is referred to as a driving pulley. A driving endless belt 50 (see FIG. 3) is extended between and wound around the driving pulley and the pulley 49. The driving endless belt 50 is circulated due to the rotation of the driving pulley, and the pulley 49 is rotated in accordance with the circulation of the driving endless belt 50 thus assisting the rotation of the entrance side roller 42. Such a constitution is advantageous in a case where torque for rotating the entrance side roller 42 is insufficient.

As shown in FIG. 2, FIG. 5 and FIG. 6, the first guide roller 39 is arranged in the strip-shaped space 36 laterally adjacent to the space 33 in a state where an upper end portion of the first guide roller 39 is slightly exposed to an upper side from the space 33 as viewed in a front view. For example, as shown in FIG. 2, the first guide roller 39 is formed of a columnar body having a diameter slightly larger than the diameter of the entrance side roller 42. In the same manner as the entrance side roller 42, the first guide roller 39 is pivotally supported in a rotatable manner about the center axis thereof within a vertical plane which is parallel to the conveyance direction F.

As shown in FIG. 2, the second guide roller 40 and the third guide roller 41 are formed of a columnar body having a diameter slightly smaller than the diameter of the entrance side roller 42, for example. In the same manner as the entrance side roller 42, the second guide roller 40 and the third guide roller 41 are pivotally supported in a rotatable manner about the center axes thereof within a vertical plane which is parallel to the conveyance direction F.

To be more specific, as shown in FIG. 2 and FIG. 5, the second guide roller 40 is arranged in the strip-shaped space 36 positioned on a lateral side of a lower end portion of the first inclined passage 25 in a state where a lower end of the second guide roller 40 is arranged at a height substantially equal to or slightly higher than an upper surface of the horizontal conveyance passage 24 as viewed in a front view. Further, as shown in FIG. 2, FIG. 5 and FIG. 4, the third guide roller 41 is arranged in the strip-shaped space 36 positioned on a lateral side of a lower end portion of the second inclined passage 26 in a state where a lower end of the third guide roller 41 is arranged at a height substantially equal to or slightly higher than an upper surface of the inspection conveyance passage 27 as viewed in a front view.

The first endless belt 30 of this embodiment is, as shown in FIG. 2 to FIG. 4, formed of an elastic circulation flat belt which has a width substantially equal to a width of the entrance side roller 42, for example. As shown in FIG. 2, the first endless belt 30 extends between and is wound around the entrance side roller 42 and the exit side roller 52 while being guided by an upper side of an outer peripheral surface of the first guide roller 39, a lower side of an outer peripheral surface of the second guide roller 40 and a lower side of an outer peripheral surface of the third guide roller 41. Accordingly, the first endless belt 30 circulates along the end of the conveyance passage 15 due to the rotation of the exit side roller 52.

As shown in FIG. 2, the second circulation mechanism 35 of this embodiment includes an entrance side driven rotary part 53, an exit side driven rotary part 54, the first guide roller 39, the second guide roller 40, the third guide roller 41, a fourth guide roller 55 and a fifth guide roller 56.

Firstly, as shown in FIG. 2 and FIG. 3, the entrance side driven rotary part 53 includes an entrance side driven roller 42', a shaft body 46', a bearing 44' and a driven gear 45'. The entrance side driven roller 42', the shaft body 46', the bearing 44' and the driven gear 45' of this embodiment are formed of members substantially equal to the members for forming the entrance side rotary part 32, that is, members for forming the entrance side roller 42, the shaft body 46, the bearing 44 and the main gear 45. The entrance side driven rotary part 53 is, as shown in FIG. 2 and FIG. 3, arranged above the entrance side rotary part 32 in a state where an upper side of an outer peripheral surface of the entrance side roller 42 and a lower side of an outer peripheral surface of the entrance side driven roller 42' are approximately brought into contact with each other or are slightly spaced apart from each other.

As shown in FIG. 3, the main gear 45 and the driven gear 45' are arranged so as to be meshed with each other. The driven gear 45' is rotated following the rotation of the main gear 45 so that the entrance side driven roller 42' is rotated in the direction opposite to the rotation of the entrance side roller 42.

The exit side driven rotary part 54 is constituted of members substantially equal to members for forming the entrance side driven rotary part 53, for example. That is, the exit side driven rotary part 54 includes an exit side driven roller 52' which is formed of members substantially equal to members for forming the entrance side driven roller 42', a shaft body (shaft body 46'), a bearing (bearing 44') and a driven gear (driven gear 45'), and the exit side driven roller 52' is pivotally supported in a rotatable manner about a center axis thereof within a vertical plane which is parallel to the conveyance direction F. Further, as shown in FIG. 2, the exit side driven rotary part 54 is arranged above the exit side rotary part 38 in a state where an upper side of an outer peripheral surface of the exit side roller 52 and a lower side of an outer peripheral surface of the exit side driven roller 52' are approximately brought into contact with each other or are slightly spaced apart from each other. Further, a main gear of the exit side rotary part 38 and a driven gear of the exit side driven rotary part 54 are arranged so as to be meshed with each other. The driven gear is rotated following the rotation of the main gear so that the exit side driven roller 52' is rotated in the direction opposite to the rotation of the exit side roller 52.

The fourth guide roller 55 and the fifth guide roller 56 are formed of constitutional elements substantially equal to the constitutional elements of the first guide roller 39, for example, and is pivotally supported in a rotatable manner about a center axis thereof within a vertical plane which is parallel to the conveyance direction F in the same manner as the first guide roller 39.

The fourth guide roller 55 which is pivotally supported in this manner is, as shown in FIG. 2, arranged at a position higher than the first guide roller 39 and close to the entrance opening 28 above the strip-shaped space 36.

Further, the fifth guide roller 56 is, as shown in FIG. 2, arranged at a height substantially equal to a height of the fourth guide roller 55 above the strip-shaped space 36 at a position close to the exit opening 29.

The second endless belt 37 is formed of an elastic circulation flat belt which has a length approximately 1.5 times as large as a length of the first endless belt 30. As shown in FIG. 2, the second endless belt 37 is wound around the entrance side roller 42', the fourth guide roller 55, the fifth guide roller 56 and the exit side roller 52' while being guided by the upper side of the outer peripheral surface of the first guide roller 39, the lower side of the outer peripheral surface of the second guide roller 40 and the lower side of the outer peripheral surface of the third guide roller 41. Accordingly, when the exit side roller 52 is rotated, the exit side driven roller 52' and the entrance side driven roller 42' are rotated so that the second endless belt 37 circulates along the edge of the conveyance passage 15.

In the conveyance mechanism 16 having such a constitution, by setting a distance between the entrance side roller 42 and the entrance side driven roller 42' and a distance between the exit side roller 52 and the exit side driven roller 52' to predetermined values respectively, it is possible to allow the first endless belt 30 and the second endless belt 37 to pass along the edge of the conveyance passage 15 while pushing an outer peripheral surface of the first endless belt 30 and an outer peripheral surface of the second endless belt 37 to each other. Accordingly, as shown in FIG. 3, the conveyance mechanism 16 of this embodiment can convey the medicine packaging envelope strip 3 along the conveyance passage 15 while clamping the side 6 of the medicine packaging envelope strip 3 using the first endless belt 30 and the second endless belt 37.

The constitution of the conveyance mechanism is not limited to the constitution of this embodiment, and the conveyance mechanism may adopt any constitution provided that the constitution allows the medicine packaging envelope strip 3 to be conveyed in a cantilever state including the constitution where the side 6 of the medicine packaging envelope strip 3 is clamped by a clip, and the clip is moved along the conveyance passage 15, for example.

The gap forming part 12 which constitutes one of essential parts of this embodiment is explained mainly in conjunction with FIG. 4 to FIG. 7.

As shown in FIG. 4 and FIG. 6, the gap forming part 12 includes the rod body 60, a biasing mechanism 61 which biases the rod body 60 upward, and an rod-body elevating/lowering mechanism 62 which elevates and lowers the rod body 60.

Firstly, the rod body 60 is formed of a columnar rod member which has a diameter approximately one third of a length of the space 33 in the conveyance direction, and a length slightly larger than the width of the medicine packaging envelope strip 3.

Further, as shown in FIG. 4 to FIG. 7, a plurality of projecting portions 63 are arranged on an outer peripheral surface of the rod body 60 in a staggered manner at predetermined intervals substantially equal to a diameter of a tablet, a diameter of a capsule or the like, for example.

The projecting portion 63 of this embodiment is, as shown in FIG. 7, formed of a synthetic-resin-made columnar body which has a size substantially one half to one fourth of a diameter of the tablet, for example and, as shown in FIG. 4, FIG. 6 and FIG. 7, four rows of projecting portions 63 are arranged on the rod body 60 along the longitudinal direction of the rod body 60. As shown in FIG. 4 and FIG. 7, the rod body 60 is arranged in the space 33 in a state where the longitudinal direction of the rod body 60 is approximately orthogonal to the conveyance direction F. To be more specific, the rod body 60 is arranged in a state where a proximal end side of the rod body 60 penetrates the above-mentioned recessed portion 68 formed in the third wall body 23 (see FIG. 4). The rod body 60 arranged in this manner is pivotally supported on a bearing 64 described later.

Here, the projecting portion is not limited to the columnar body, and the projecting portion may be formed of a bulging body which bulges from the peripheral surface of the columnar rod member. Further, a size of the projecting portion and an interval between the projecting portions may be arbitrarily set depending on a shape, a size and the like of tablets accommodated in the medicine packaging envelope strip 3.

The biasing mechanism 61 of this embodiment includes, as shown in FIG. 4 and FIG. 5, a support strut 65, a rod-body support block 66 and an elastic member 67 formed of a tensile coil spring or the like.

As shown in FIG. 4 and FIG. 5, the support strut 65 of this embodiment is formed of a strip-shaped flat plate member which has a length substantially equal to a length from the support plate 201 to the space 33. The support strut 65 is mounted on the support plate 201 in an upright state at a position corresponding to an intermediate portion of the first inclined passage 25 and on a slightly viewer's side from the third wall body 23. Further, as shown in FIG. 4 and FIG. 5, a columnar shaft portion 69 is mounted on the support strut 65 at a position slightly below an upper end of the support strut 65 and the shaft portion 69 projects toward the viewer's side. Further, as shown in FIG. 4 and FIG. 5, an engaging projection 70 with which an elastic member 67 described later is engaged is mounted on the support strut 65 at a position in the vicinity of the center of the support strut 65 and the engaging projection 70 projects in the viewer's direction.

As shown in FIG. 4 and FIG. 5, the rod-body support block 66 is formed of a rectangular-parallelepiped block member having a length slightly larger than a length of the first inclined passage 25, for example. Further, as shown in FIG. 4 and FIG. 5, the shaft portion 69 penetrates an approximately longitudinally-center portion of the rod-body support block 66 such that the longitudinal direction of the rod-body support block 66 is substantially directed to the conveyance direction F whereby the rod-body support block 66 is pivotally and rotatably supported on the support strut 65 about the shaft portion 69 within a vertical plane which is parallel to the conveyance direction F.

Further, as shown in FIG. 4 and FIG. 5, the bearing 64 formed of a roller bearing or the like, for example, is provided to one end side of the rod-body support block 66, and the rod-body support block 66 pivotally and rotatably supports the rod body 60 by way of the bearing 64. Further, as shown in FIG. 4 and FIG. 5, an engaging projection piece 71 with which the elastic member 67 described later is engaged is mounted on the rod-body support block 66 at a position close to the other end of the rod-body support block 66 in a state where the engaging projection piece 71 projects toward the viewer's side. Further, the other end portion 83 of the rod-body support block 66 is elevated or lowered while keeping contact with an upper surface of an elevating/lowering block 73 described later and hence, the other end portion 83 is chamfered in a semispherical shape for ensuring the smooth elevation and lowering of the rod-body support block 66.

Next, as shown in FIG. 4 and FIG. 5, the elastic member 67 is formed of a coil spring having a predetermined length, for example, and one end of the elastic member 67 is engaged with the engaging projection 70 and the other end of the elastic member 67 is engaged with the engaging projection piece 71.

Figure 5A:
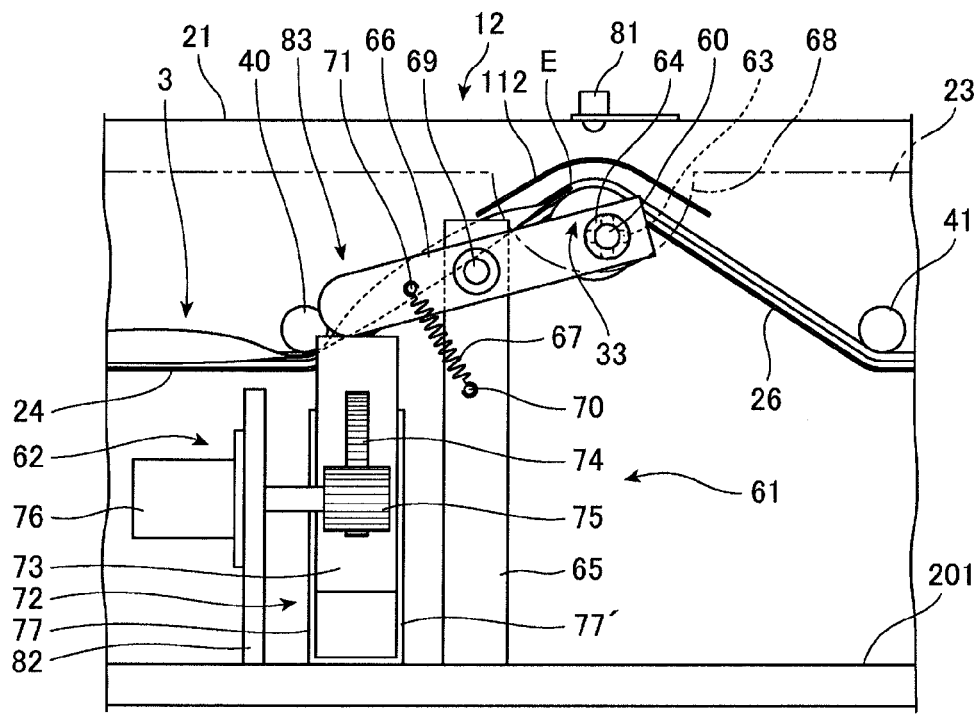
FIG. 5 is a front view for explaining an operation of the gap forming part of the tablet inspecting device according to the embodiment of the present invention.
Figure 5B:
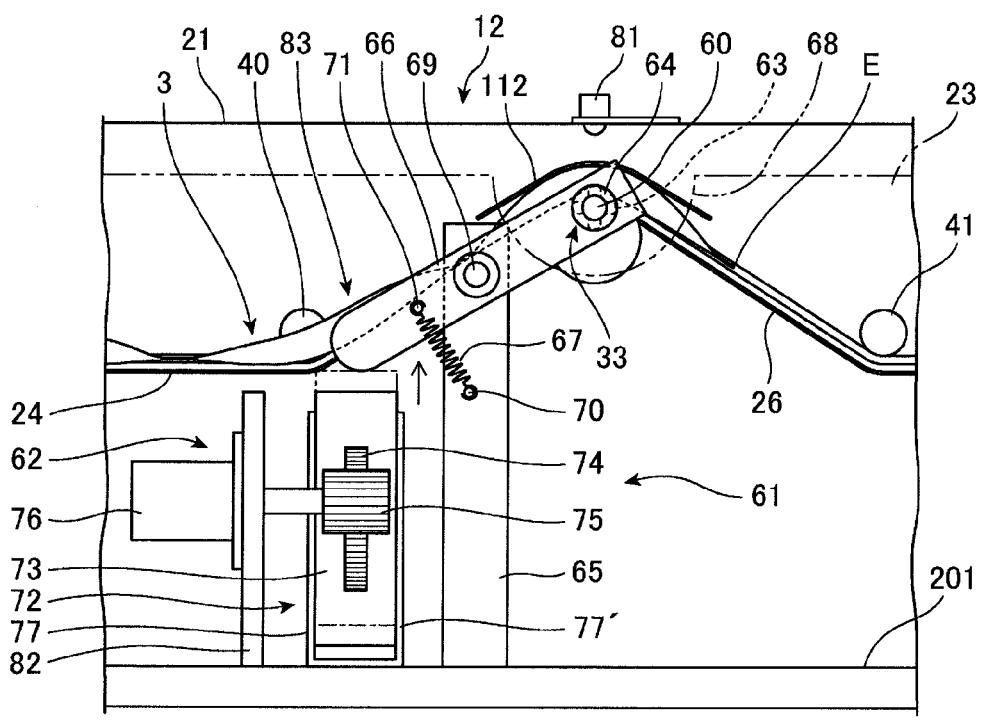

As shown in FIG. 4 and FIG. 5, a natural length of the elastic member 67 (a length of the elastic member 67 when force is not applied to the elastic member 67) is set to a length which allows the bearing 64 mounted on the rod-body support block 66 to be positioned at a height substantially equal to a height of the space 33. To be more specific, the length of the elastic member 67 is set to a length which makes an upper side of an outer peripheral surface of the rod body 60 which is pivotally supported as described later positioned at a height substantially equal to a height of an upper side of an outer peripheral surface of the first guide roller 39. Further, the natural length of the elastic member 67 is set to a length which makes the rod-body support block 66 inclined upward in the conveyance direction F. The other end side of the rod-body support block 66 is always biased downward by the elastic member 67. Hereinafter, a position of the rod body 60 which is restricted by the elastic member 67 with the natural length is referred to as a home position (see FIG. 5B).

As shown in FIG. 4 and FIG. 5, a viewer's side of the above-mentioned rod body 60 is pivotally supported on the bearing 64 so that the rod body 60 is rotatably supported about a longitudinally extending center axis thereof, and the rod body 60 is always biased upward by the biasing mechanism 61.

As shown in FIG. 4 and FIG. 5, the rod-body elevating/lowering mechanism 62 includes a guide frame 72, the elevating/lowering block 73, a pinion 75, a rack 74 which meshes with the pinion 75, a rotary unit 76 for rotating the rack 74 and a medicine packaging envelope strip detecting sensor 81.

As shown in FIG. 4 and FIG. 5, the guide frame 72 is formed of strip-shaped flat plate members each of which has a height slightly smaller than a height of the horizontal conveyance passage 24 from the support plate 201, for example. The guide frame 72 includes flat plate members 77, 77' which are arranged so as to face each other in an opposed manner with a predetermined distance therebetween in a state where plate surfaces of these members 77, 77' are arranged orthogonal to the conveyance direction F. As shown in FIG. 4, a longitudinally elliptical guide hole 79 for guiding a projection piece 78 described later is opened in the flat plate members 77, 77' respectively.

The guide frame 72 which is formed in this manner is, as shown in FIG. 4 and FIG. 5, mounted on the support plate 201 in an upright manner at a position below the other-end portion 83 of the rod-body support block 66.

Next, as shown in FIG. 4 and FIG. 5, the elevating/lowering block 73 is formed of a rectangular-parallelepiped block body which is fitted in a space defined between the flat plate member 77 and the flat plate member 77'. Further, elevating/lowering block 73 is arranged in the space defined between the flat plate member 77 and the flat plate member 77' in such a manner that the block 73 can be elevated and lowered. Further, as shown in FIG. 4, the elevating/lowering block 73 is arranged in a state where the projection piece 78 is mounted on a side surface of the elevating/lowering block 73 which is brought into contact with the flat plate member 77' in a projecting manner, and the projection piece 78 is inserted into the guide hole 79.

Further, as shown in FIG. 4 and FIG. 5, the elevating/lowering block 73 includes the rack 74 formed of an elongated spur gear, for example. As shown in FIG. 4 and FIG. 5, the rack 74 is fixedly mounted on a viewer's side surface of the elevating/lowering block 73 in a state where the longitudinal direction of the rack 74 extends in the vertical direction.

Next, as shown in FIG. 4 and FIG. 5, the pinion 75 is formed of a columnar gear, for example, is pivotally and rotatably supported on a fixed plate 82 which is mounted on the support plate 201 in an upright manner, and is meshed with the rack 74.

The rotary unit 76 is formed of a motor such as a stepping motor, for example, is fixedly mounted on the fixed plate 82, and rotates the pinion 75 as shown in FIG. 4 and FIG. 5.

In the rod-body elevating/lowering mechanism 62 having such a constitution, the elevating/lowering block 73 provided with the rack 74 is elevated and lowered by rotating the pinion 75 by the rotary unit 76.

The medicine packaging envelope strip detecting sensor 81 is formed of a known optical sensor and, as shown in FIG. 4 and FIG. 5, is arranged above the space 33 and detects the medicine packaging envelope strip 3 which passes below the medicine packaging envelope strip detecting sensor 81.

The tablet inspecting device 10 of this embodiment includes a control part (not shown in the drawing) which is constituted of a CPU, a timer, a memory part and the like. The control part controls the rotary unit 76 upon receiving a signal from the medicine packaging envelope strip detecting sensor 81.

Here, an example of the manner of operation of the rod-body elevating/lowering mechanism 62 is explained in conjunction with FIG. 5A and FIG. 5B. FIG. 5A shows a state where the rod body 60 is lowered, and FIG. 5B shows a state where the rod body 60 is elevated. For example, before the medicine packaging envelope strip 3 is conveyed to the gap forming part 12, as shown in FIG. 5A, the elevating/lowering block 73 is elevated so that an upper surface 84 of the elevating/lowering block 73 pushes up the other end portion 83 of the rod-body support block 66 while keeping contact with the other end portion 83 of the rod-body support block 66. Due to such an operation, the rod-body support block 66 is rotated about the shaft portion 69 against an elastic force, that is, a biasing force of the elastic member 67 so that the rod body 60 is lowered. Here, the rod-body elevating/lowering mechanism 62 lowers the rod body 60 to a predetermined height where the rod body 60 does not obstruct passing of a distal end E of the medicine packaging envelope strip 3 through the space 33.

When the medicine packaging envelope strip 3 is conveyed in the conveyance direction F so that, for example, the distal end E of the medicine packaging envelope strip 3 passes the center of the space 33, the medicine packaging envelope strip detecting sensor 81 detects the distal end E of the medicine packaging envelope strip 3, and transmits a detection signal to the control part. Upon receiving the detection signal, the control part lowers the elevating/lowering block 73 after a lapse of a predetermined time that the distal end E passes an upper end of the second inclined passage 26 after the detection of the signal, for example. Due to lowering of the elevating/lowering block 73, as shown in FIG. 5B, the elastic member 67 returns to the natural length and the rod body 60 is elevated. When the elevating/lowering block 73 is further lowered, as shown in FIG. 5B, the upper surface 84 of the elevating/lowering block 73 is separated from the other end portion 83 of the rod-body support block 66 and the rod body 60 takes the home position.

Figure 6A:
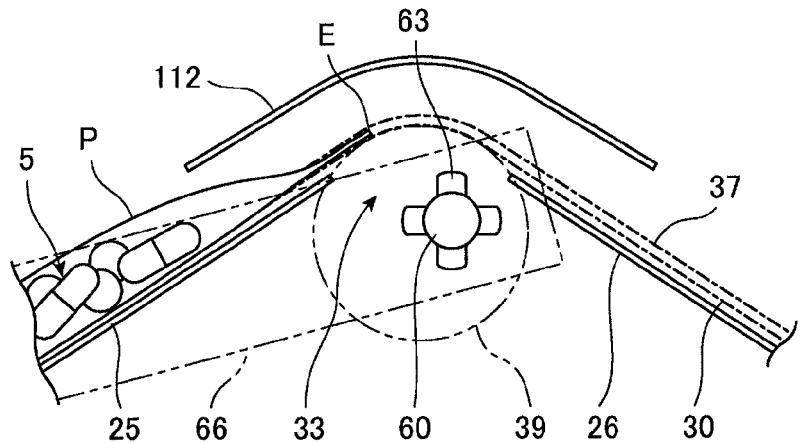
FIG. 6 is a front view of an essential part for explaining the operation of the gap forming part of the tablet inspecting device according to the embodiment of the present invention.
Figure 6B:
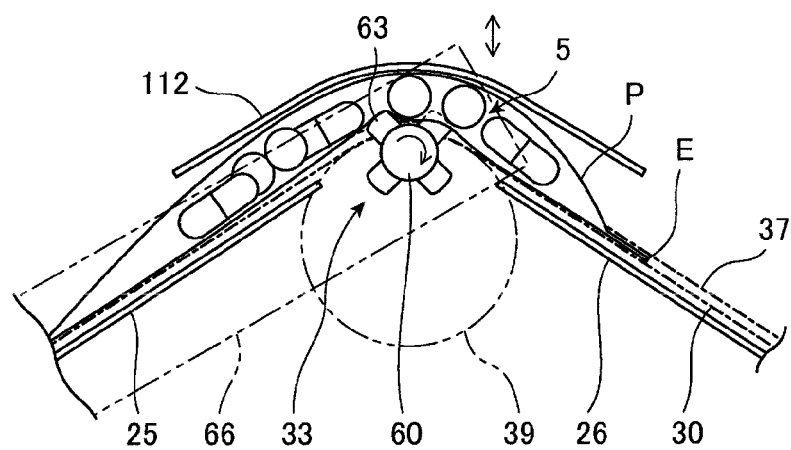
Figure 6C:
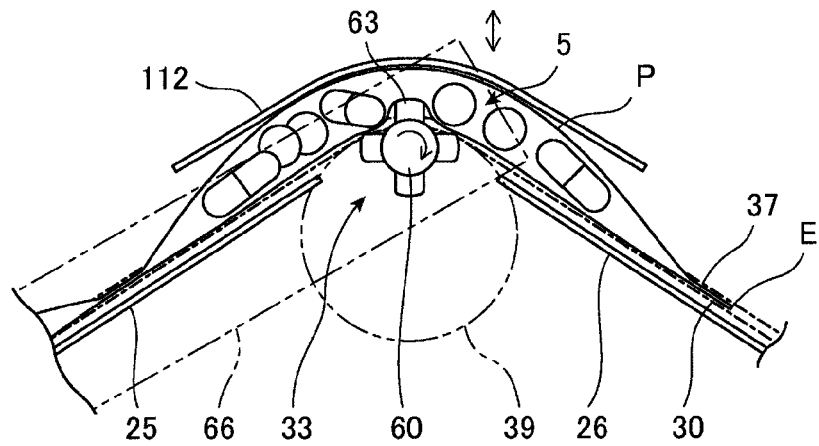
Figure 7A:
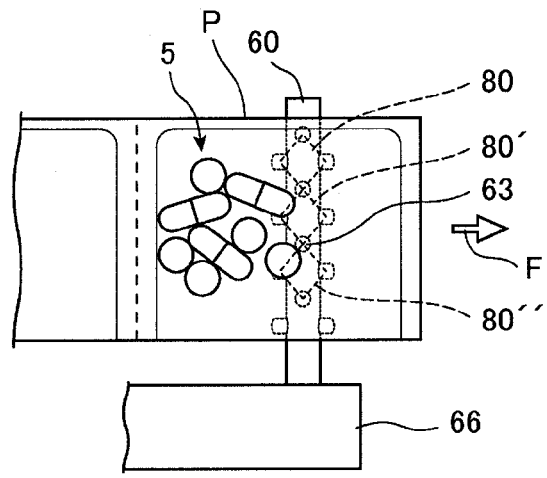
FIG. 7 is a plan view of an essential part for explaining the operation of the gap forming part of the tablet inspecting device according to the embodiment of the present invention.
Figure 7B:
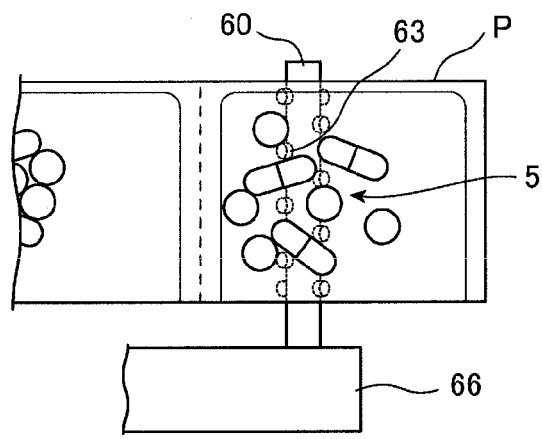
Figure 7C:
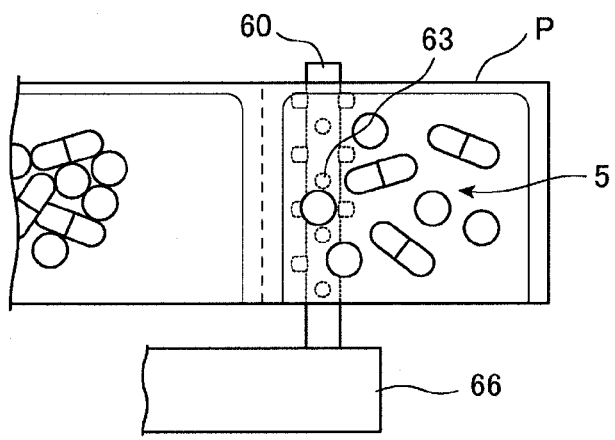

Here, an example of manner of operation of the gap forming part 12 of this embodiment is explained in conjunction with FIG. 6 and FIG. 7. FIG. 6A shows a state where the distal end of the medicine packaging envelope strip 3 almost reaches the space 33, and FIG. 6B and FIG. 6C show a state where the medicine packaging envelope strip 3 is conveyed over the rod body 60. FIG. 7 is an explanatory plan view of an essential part for explaining a mode for forming a gap between the tablets, and shows a mode where one tablet packaging envelop P is conveyed in order of steps shown in FIG. 7A, FIG. 7B and FIG. 7C.

As shown in FIG. 6A, when the distal end E of the medicine packaging envelope strip 3 almost reaches the space 33, the rod body 60 is lowered by the rod-body elevating/lowering mechanism 62 as described above so that the rod body 60 is arranged slightly below the first endless belt 30. Next, when the distal end E of the medicine packaging envelope strip 3 gets over the space 33 and almost reaches the second inclined passage 26, as shown in FIG. 6B, the rod body 60 is elevated to the home position by the rod-body elevating/lowering mechanism 62.

Then, as shown in FIG. 6B and FIG. 6C, the medicine packaging envelope strip 3 is conveyed while being pushed to the rod body 60 from above, and the rod body 60 is rotated. In other words, the rod body 60 is rotated when the medicine packaging envelope strip 3 passes over the rod body 60 while being brought into contact with the rod body 60. Here, FIG. 6C shows a state where the rod body 60 is slightly further rotated from a state shown in FIG. 6B.

Here, as shown in FIG. 6B, and FIG. 6C, the projecting portion 63 forcibly enters between adjacent tablets thus separating the tablets from each other. Further, the projecting portions 63 are arranged in a staggered manner and hence, as shown in FIG. 7B, the projecting portions 63 can separate the adjacent tablets from each other not only in the widthwise direction (short side direction) of the medicine packaging envelope strip 3 but also in the conveyance direction F. To explain in detail, as shown in FIG. 7A, the adjacent tablets can be separated from each other in such a manner that one tablet is caught by each lattice 80, 80', 80", . . . formed by a plurality of (4 in this embodiment) projecting portions 63 arranged in a staggered manner.

In this manner, in the gap forming part 12 of this embodiment, the medicine packaging envelope strip 3 is conveyed over the rod body 60 while rotating the rod body 60 so that a gap is formed between the adjacent tablets by way of the projecting portions 63.

Further, a rod body 60 is upwardly biased by the elastic member 67 and hence, the rod body 60 is vertically tilted around the shaft portion 69 corresponding to a size, a posture or a weight of tablets accommodated in a medicine packaging envelope strip 3. Accordingly, the gap forming part 12 can prevent breaking of the medicine packaging envelope, the deformation of tablets, the occurrence of flaws on the tablets or the like attributed to a phenomenon that an excessively large force is applied to a bottom surface of the medicine packaging envelope strip 3 from the projecting portion when the rod body is rotated. Further, the gap forming part 12 can assist the entrance of the projecting portion 63 into a space defined between the adjacent tablets corresponding to the delicate difference in a state of a bottom surface of the medicine packaging envelope strip 3 due to a size of the tablets, an accommodated state of the tablets, a weight of the tablets or the like.

Next, the flipping mechanism 14 which constitutes one of essential parts of this embodiment is explained in conjunction with mainly FIG. 3, FIG. 8 and FIG. 9.

The flipping mechanism 14 of this embodiment includes, as shown in FIG. 8 and FIG. 9, leaf springs 92 each of which is constituted of an elongated resilient member and a hammer portion 99.

Firstly, as shown in FIG. 3, FIG. 8 and FIG. 9, the leaf spring 92 has a width which is approximately one fourth of width of the folded side 2 of the medicine packaging envelope P and has a predetermined length, and is formed of a metal-made resilient strip-shaped thin plate member, for example. In the flipping mechanism 14 of this embodiment, as shown in FIG. 3, FIG. 8 and FIG. 9, two leaf springs 92, 92' extend downward vertically toward a side portion of the flat conveyance passage in a state where plate faces of the respective leaf springs 92, 92' face a horizontal conveyance passage 24 side and are slightly spaced apart from each other in the conveyance direction F. To be more specific, as shown in FIG. 3, FIG. 8 and FIG. 9, the leaf springs 92, 92' have an upper end side thereof supported on an arm plate 100 which projects in the conveyance direction from an upper end portion of a support plate 96 which is mounted on the support plate 201 in an upright manner, and the leaf springs 92, 92' are arranged between the second wall body 22 and the third wall body 23. A lower end side of the leaf springs 92, 92' forms free ends at a position slightly spaced apart in the horizontal direction from a side portion (folded side 2 side) of the medicine packaging envelope strip 3.

With respect to the leaf springs 92, 92' of this embodiment, as shown in FIG. 3 and FIG. 9, for example, plate-shaped buffer members 103, 103' having a thickness approximately 3 times as large as a thickness of the leaf springs 92, 92' and a length approximately half of a length of the leaf springs 92, 92' are mounted on lower end portions of plate surfaces of leaf springs 92, 92' on a medicine packaging envelope strip 3 side. The buffer members 103, 103' are formed of a synthetic resin elastic member, for example, and function as buffer means for preventing breaking of the medicine packaging envelope strip 3 or the like when the leaf springs 92, 92' flip a side portion of the medicine packaging envelope strip 3 as described later.

Next, as shown in FIG. 3, FIG. 8 and FIG. 9, the hammer portion 99 includes a drum body 90, a drive portion 91 and projecting members 97.

As shown in FIG. 3, FIG. 8 and FIG. 9, the drum body is formed of a columnar body which has a diameter approximately half of a strip width of the medicine packaging envelope strip 3 and a length slightly smaller than a length of the folded side 2 of the medicine packaging envelope P and a shaft member 95 which projects along a center axis 94 of the columnar body from one end surface of the columnar body, for example.

As shown in FIG. 3 and FIG. 8, in a state where the center axis 94 is directed in the approximately conveyance direction F, the drum body 90 is arranged below and in the vicinity of the leaf spring 92. To be more specific, as shown in FIG. 3 and FIG. 8, the drum body 90 of this embodiment is arranged between the second wall body 22 and the third wall body 23 and slightly below the horizontal conveyance passage 24 as viewed in a front view.

The drive portion 91 is formed of the electrically-operated motor such as a stepping motor, for example, and is supported on a support plate 96 and is connected to the shaft member 95 thus rotating the drum body 90 as shown in FIG. 8. Here, as shown in FIG. 9, the drive portion 91 rotates the drum body 90 about the center axis 90 in a counter clockwise direction as viewed in a right side view. The drive portion 91 is configured to be driven in response to an instruction from the above-mentioned control part.

Next, as shown in FIG. 3, FIG. 8 and FIG. 9, each projecting member 97 is, for example, formed of a half split columnar body having an approximately semicircular cross-sectional shape obtained by splitting, in the longitudinal direction, a columnar body having a length substantially equal to a diameter of the drum body 90 and a diameter approximately one fourth to one third of a length of the drum body 90. In the flipping mechanism 14 of this embodiment, as shown in FIG. 3, FIG. 8 and FIG. 9, for example, four projecting members 97a, 97b, 97c, 97d project radially from a trunk portion 98 of the drum body 90. To be more specific, as shown in FIG. 3, FIG. 8 and FIG. 9, out of four projecting members, two projecting members 97a, 97b are arranged to face each other in an opposed manner with the center axes 94 sandwiched therebetween below the leaf spring 92'. Further, two other projecting members 97c, 97d are arranged below the leaf spring 92 in a mode where the projecting members 97a, 97b are rotated by approximately 90 degrees about the center axis 94.

An operation example of the flipping mechanism 14 of this embodiment is explained in conjunction with FIG. 9.

Figure 9A:
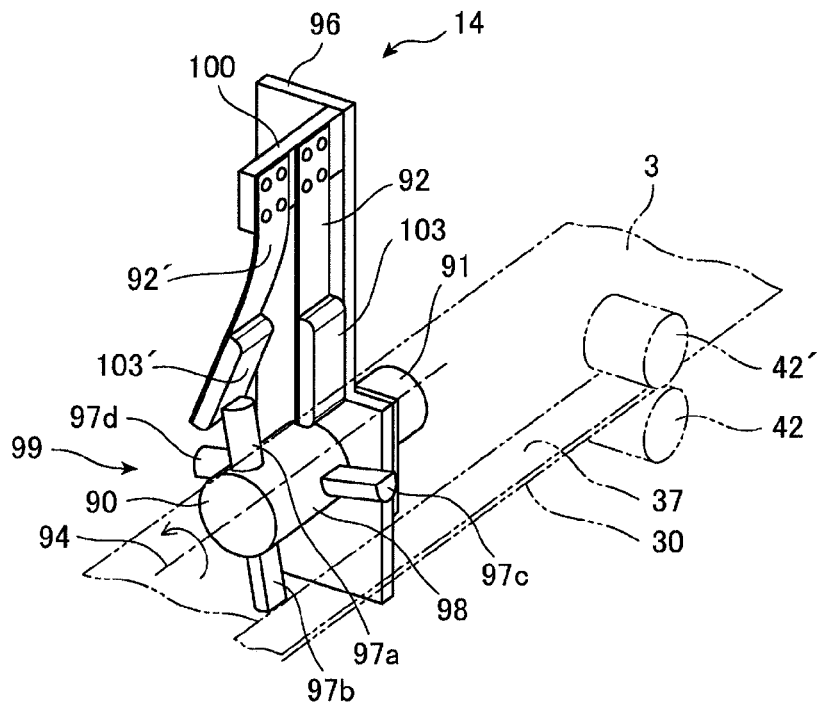
FIG. 9 is a perspective view for explaining an operation of the flipping mechanism of the tablet inspecting device according to the embodiment of the present invention.
Figure 9B:
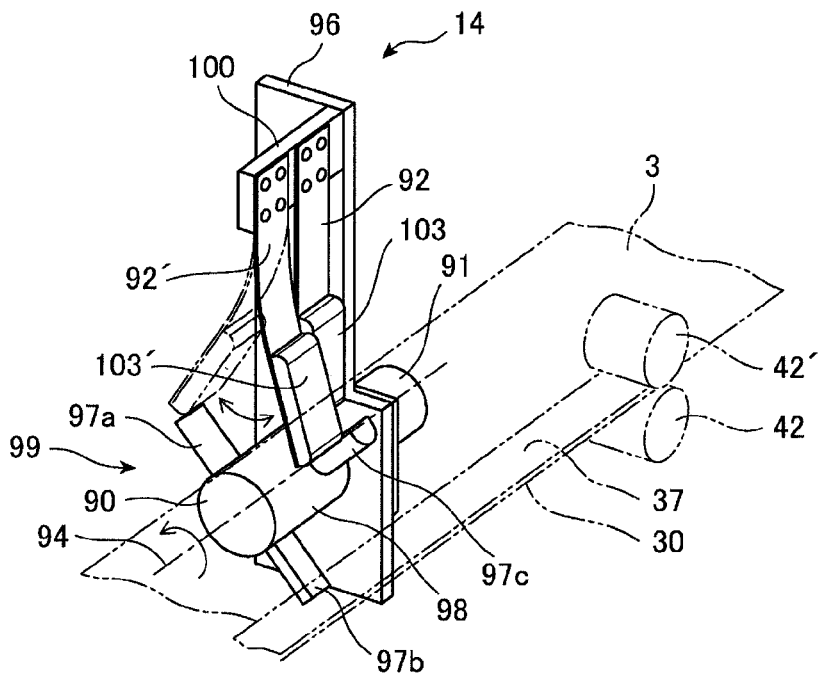

Firstly, the drive portion 91 is rotated by operating a start button (not shown in the drawing) of the tablet inspecting device 10, for example. Due to the rotation of the drive portion 91, as shown in FIG. 9A, the drum body 90 is rotated so that, for example, the projecting member 97a is brought into contact with the buffer member 103' and resiliently deforms a lower end portion of the leaf spring 92'. To be more specific, as shown in FIG. 9A, the lower end portion of the leaf spring 92' is bent in the direction which is the direction approximately orthogonal to the conveyance direction F and also is the direction that the lower end portion is separated from the medicine packaging envelope strip 3. When the drum body 90 is further rotated, as shown in FIG. 9B, the projecting member 97a is disengaged from the lower end portion of the leaf spring 92', and flips a folded side 2 side of the medicine packaging envelope strip 3 when the lower end portion returns to an original position from a resiliently deformed position. When the drum body 90 is further rotated, the projecting member 97c resiliently deforms the lower end portion of the leaf spring 92, and flips a folded side 2 side of the medicine packaging envelope strip 3 when the leaf spring 92 returns to the original position from the resiliently deformed position in the same manner.

In this manner, the leaf springs 92, 92' alternately flip the folded side 2 side of the medicine packaging envelope strip 3 during the rotation of the drum body 90 so that tablets in the medicine packaging envelope strip 3 can be scattered. When the leaf springs 92, 92' return to the original position from the resiliently deformed position, the leaf springs 92, 92' can move while slightly entering the inside through the notch 102 in the above-mentioned manner and hence, the movement of the leaf springs 92, 92' can be ensured.

As described above, the hammer portion 99 is configured to intermittently resiliently deform the leaf springs 92, 92' in the direction approximately orthogonal to the conveyance direction F.

The above-mentioned elongated resilient members are not limited to the leaf springs 92, 92', and the elongated resilient members may be formed of a rod-like spring member having resiliency.

Figure 10:
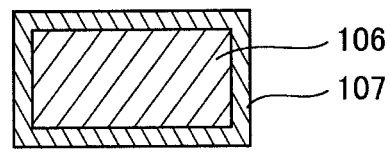
FIG. 10 is a cross-sectional view taken along a line B-B in FIG. 2.

Next, the overlapping releasing part 13 which constitutes one of essential parts of this embodiment is explained in conjunction with mainly FIG. 2, FIG. 10 and FIG. 11.

As shown in FIG. 2 and FIG. 11, the overlapping releasing part 13 of this embodiment includes a rotary body 104, a bearing 105, an elevating/lowering plate member 106, and an elevating/lowering guide member 107.

Firstly, as shown in FIG. 2 and FIG. 11, the rotary body 104 is formed of a resilient columnar body which has a length equal to a strip width of the medicine packaging envelope strip 3 and a diameter approximately half of the above-mentioned folded side 2, for example. As shown in FIG. 11, a shaft rod 109 is mounted on one end of the rotary body 104 such that the shaft rod 109 projects from a center portion of one end surface in the direction of an center axis 108. As shown in FIG. 11, the rotary body 104 is arranged above the horizontal conveyance passage 24 with a predetermined gap D therebetween in a state where the center axis 108 is approximately orthogonal to the conveyance direction F.

It is preferable that the rotary body 104 has a weight to an extent that the rotary body 104 is not elevated following an upper-side tablet among tablets in an overlapped state when the medicine packaging envelope strip 3 passes between the horizontal conveyance passage 24 and the rotary body 104. This is because when the rotary body 104 is lifted following the upper-side tablet, it is difficult to release overlapping of the tablets. Further, it is preferable that the rotary body 104 is formed of a material having elasticity such as a sponge, for example. This is because such a material does not apply an excessively large force to the tablets.

Next, as shown in FIG. 2 and FIG. 10, the elevating/lowering guide member 107 is formed of a hollow cylindrical body having a height equal to a height from the support plate 201 to the horizontal conveyance passage 24, having a rectangular shape in cross section, and having an upper end thereof open ended. The elevating/lowering guide member 107 is, as shown in FIG. 2, mounted on the support plate 201 in an upright manner in front of the second wall body 22 and in the vicinity of the entrance opening 28.

The elevating/lowering plate member 106 is, as shown in FIG. 11 and FIG. 10, formed of a rectangular parallelepiped block which has a length approximately 1.2 times as large as a length of the elevating/lowering guide member 107 and is fitted into a hollow portion of the elevating/lowering guide member 107, for example. The elevating/lowering plate member 106 is elevatably and loosely inserted into the hollow portion of the elevating/lowering guide member 107.

As shown in FIG. 2 and FIG. 11, a bearing 105 is mounted on an upper end side of the elevating/lowering plate member 106 having such constitution, and the shaft rod 109 of the above-mentioned rotary body 104 is rotatably and pivotally supported. An opening (not shown in the drawing) is formed in the first wall body 21, wherein the opening allows the penetration of the shaft rod 109 therethrough and does not become an obstacle in elevation/lowering of the shaft rod 109.

As explained above, as shown in FIG. 11, the rotary body 104 of this embodiment is rotatably and pivotally supported about the center axis 108, and also can be elevated or lowered.

The rotary body 104 may not be limited to the columnar body of this embodiment and may be formed of a cylindrical body.

Next, an example of the manner of operation of the overlapping releasing part 13 is explained in conjunction with FIG. 11.

Figure 11A:
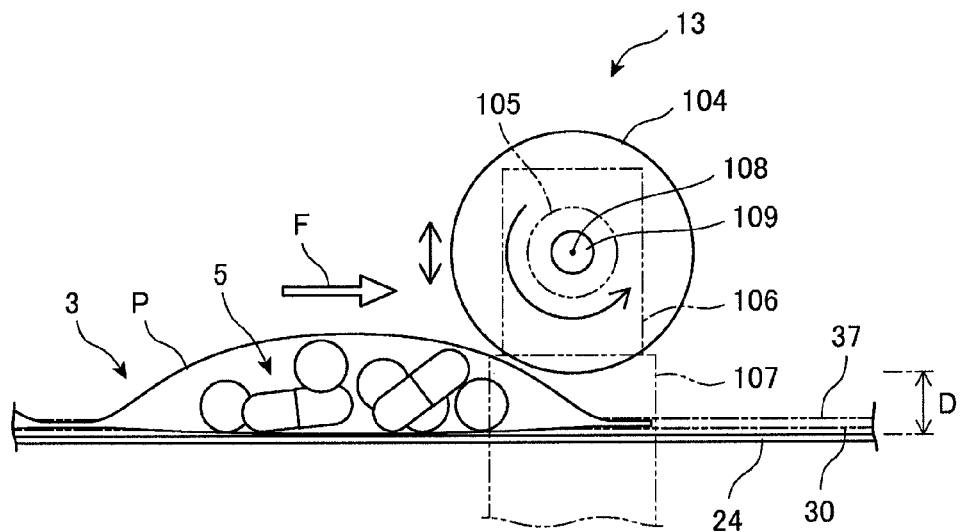
FIG. 11 is a front view of an essential part for explaining an operation of an overlapping releasing part of the tablet inspecting device according to the embodiment of the present invention.
Figure 11B:
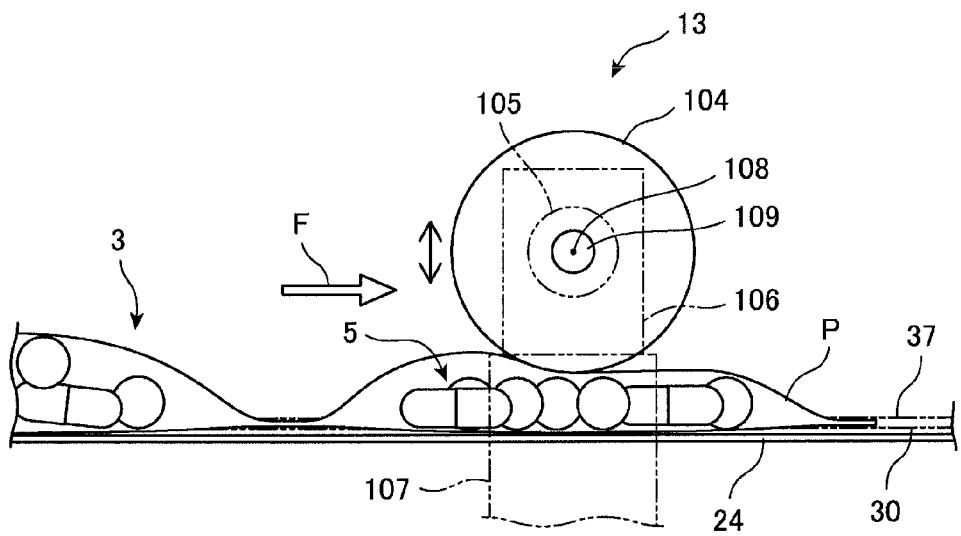

As shown in FIG. 11A, during the conveyance of the medicine packaging envelope strip 3 between the horizontal conveyance passage 24 and the rotary body 104, as shown in FIG. 11B, out of tablets overlapped vertically, an upper-side tablet is pushed by the rotary body 104 so that the upper-side tablet slides down whereby overlapping of the tablets is released. In this manner, when the medicine packaging envelope strip 3 passes between the horizontal conveyance passage 24 and the rotary body 104, overlapping of the tablets 5 accommodated in a vertically overlapped state in the medicine packaging envelope strip 3 can be released.

As shown in FIG. 2, the tablet inspecting device 10 of this embodiment is provided with the overlapping releasing part 13' having the substantially same constitution as the overlapping releasing part 13 in the vicinity of a downstream end of the horizontal conveyance passage 24.

Next, the inspecting part 300 of this embodiment is arranged below an opening of the above-mentioned inspection conveyance passage 27, and includes, for example, a light source which irradiates infrared rays or the like (not shown in the drawing), a camera 301 which is arranged above the opening, a support strut 302 which supports the camera 301 thereon, an image processing unit, a CPU and the like. The camera 301 images a transmission image of the medicine packaging envelope P using light radiated from the light source, and the number of tablets can be counted by automatically counting the number of silhouette images of the tablets appearing in the transmission image.

The inspecting part is not limited to the inspecting part 300 which performs image processing of the silhouette images of the tablets as in the case of this embodiment, and may discriminate tablets by imaging reflection images of tablets using two sets of cameras and restores three-dimensional shapes of the tablets from the reflection images by making use of parallax between two sets of cameras, for example.

As shown in FIG. 2, FIG. 4, FIG. 5 and FIG. 6, the tablet inspecting device 10 of this embodiment includes a guide plate 112 having an approximately inverse-V-shape as viewed in a front view above the space 33. As shown in FIG. 4 and FIG. 5, the guide plate 112 is arranged such that a crest portion which is formed in an upwardly projecting shape is positioned above the center of the space 33, and the guide plate 112 is supported on the third wall body 23. Even when a portion of a distal end E of the medicine packaging envelope strip 3 is curled up when the medicine packaging envelope strip 3 gets over the space 33, for example, the guide plate 112 guides the curled-up portion such that the medicine packaging envelope strip 3 can smoothly get over the space 33 whereby the medicine packaging envelope strip 3 can be smoothly conveyed. That is, the guide plate 112 is a guide unit which guides the distal end of the medicine packaging envelope strip 3. Particularly, with respect to the distal end E of the medicine packaging envelope strip 3, there exists a possibility that a folded side 2 of the medicine packaging envelope strip 3 which is not sandwiched or clamped by the first endless belt 30 and the second endless belt 37 is curled up and hence, it is effective to arrange the guide plate 112 above the folded side 2 side.

Next, an example of the manner of the whole operation of the tablet inspecting device 10 of this embodiment is explained in conjunction with FIG. 1 to FIG. 12. FIG. 12A shows an example where the tablets 5 are accommodated after medicine packaging envelope strip 3 passes the flipping mechanism 14, and FIG. 12B shows an example where the tablets 5 are accommodated after the medicine packaging envelope strip 3 passes the gap forming part 12.

Firstly, before the medicine packaging envelope strip 3 is supplied to the tablet inspecting device 10, as described previously, to prevent the rod body 60 from becoming an obstacle when the distal end E of the medicine packaging envelope strip 3 gets over the space 33, the rod body 60 is lowered by the rod body elevating/lowering mechanism 62 (see FIG. 5A, FIG. 6A).

Then, when an operator pushes the above-mentioned start button, for example, as shown in FIG. 1, the medicine packaging envelope strip 3 in which a plurality of tablets are accommodated in a state where the tablets are collected non-uniformly on a folded side 2 side of the medicine packaging envelope P is conveyed over the guide passage 110, and is supplied to the tablet inspecting device 10 from the entrance opening 28. To be more specific, as shown in FIG. 2 and FIG. 3, the medicine packaging envelope strip 3 is conveyed onto the conveyance passage 15 in a state where the medicine packaging envelope strip 3 is sandwiched between the second endless belt 37 and the first endless belt 30 which pass between the entrance side roller 42 and the entrance side driven roller 42'. Here, as shown in FIG. 11, overlapping of the tablets accommodated in a vertically overlapped state is released by the overlapping releasing part 13 arranged in the vicinity of the entrance opening 28.

Figure 12A:
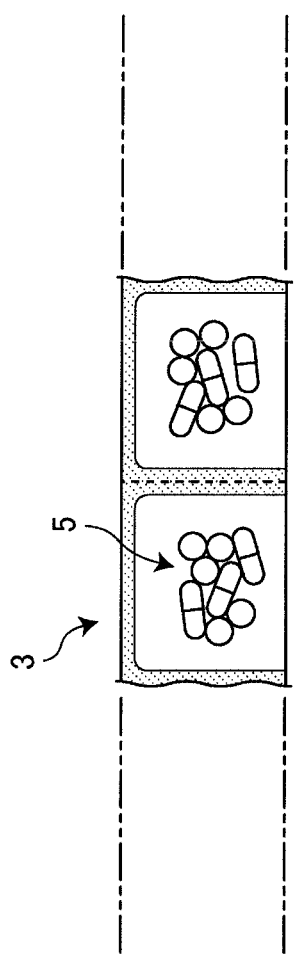
FIG. 12 is an explanatory plan view of the tablet inspecting device according to the embodiment of the present invention.

Next, the folded side 2 side of the medicine packaging envelope strip 3 conveyed to a position corresponding to the flipping mechanism 14 is, as shown in FIG. 9, flipped by the leaf springs 92, 92' and hence, as shown in FIG. 12A, the tablets which are densely collected on the folded side 2 side, for example, are scattered in the short-side direction (widthwise direction) of the medicine packaging envelope strip 3.

Then, when the tablets vertically overlap with each other again after the medicine packaging envelope strip 3 passes the flipping mechanism 14, the overlapping of the tablets is released by the overlapping releasing part 13' in the same manner.

Next, when the medicine packaging envelope strip 3 is conveyed along the first inclined passage 25, the tablets 5 slide down so that the tablets 5 are collected in an area close to an upstream side in the medicine packaging envelope P as shown in FIG. 7A.

Then, when the distal end E of the medicine packaging envelope strip 3 gets over the space 33 and almost reaches the upper end of the second inclined passage 26, for example, the rod body 60 is elevated to the home position by the rod body elevating/lowering mechanism 62 (see FIG. 5B, FIG. 6B). When the medicine packaging envelope strip 3 is conveyed over the rod body 60 while rotating the rod body 60 (see FIG. 6B, FIG. 6C), the tablets 5 are slightly separated from each other by the projecting portions 63 (see FIG. 7B). Then, when the medicine packaging envelope strip 3 is further conveyed, as shown in FIG. 7C, the tablets slip down to a downstream side along the second inclined passage 26 so that the tablets are further scattered.

In such a state, the rod body 60 is resiliently biased upward and hence, the rod body 60 is resiliently tilted vertically corresponding to sizes, postures or weights of the accommodated tablets whereby it is possible to prevent an extremely large force from being applied to the tablets or the medicine packaging envelope strip 3.

Further, since the tablets 5 can be scattered in the longitudinal direction of the rod body 60 by the flipping mechanism 14, the gap forming part 12 can easily form gaps.

Figure 12B:
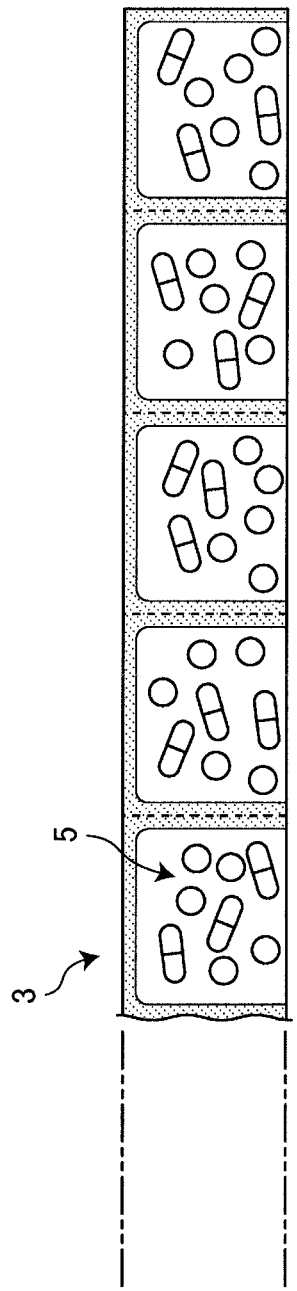

The tablets conveyed to the inspecting part 300 after passing through the gap forming part 12 are brought into a scattered state shown in FIG. 12B. Accordingly, a close-contact state of the tablets in silhouette images imaged by the inspecting part 300 can be eliminated and hence, the number of tablets can be accurately counted. Further, the contact between the tablets can be also eliminated in the reflection images of the tablets and hence, the tablets can be easily recognized one by one thus overcoming the difficulty in discriminating tablets.

As has been explained above, according to the tablet inspecting device 10 of this embodiment, an error in counting tablets and the difficulty in discriminating tablets which are generated due to the close contact of the tablets accommodated in the medicine packaging envelope can be eliminated and hence, it is possible to provide the tablet inspecting device which can accurately inspect the tablets.

Although several embodiments of the present invention have been explained in detail based on the drawings, there embodiments are merely examples, and the present invention can be carried out in other modes to which various modifications and improvements are applied based on knowledge of those who are skilled in the art.

What is claimed is:

1. A tablet inspecting device in which a medicine packaging envelope strip which is formed in a strip shape by continuously connecting a plurality of medicine packaging envelopes each of which accommodates tablets in the inside thereof and is separated when a user takes the tablets is imaged thus inspecting the tablets in the inside of the medicine packaging envelope, the tablet inspecting device comprising:
   a conveyance passage along which the medicine packaging envelope strip placed thereon is conveyed in the longitudinal direction of the medicine packaging envelope strip;
   a conveyance mechanism which conveys the medicine packaging envelope strip along the conveyance passage; and
   a gap forming part which forms a gap between the adjacent tablets, wherein
   the conveyance passage includes:
   a horizontal conveyance passage along which the medicine packaging envelope strip is conveyed in an approximately horizontal state;
   a first inclined passage with upward inclination which extends from the horizontal conveyance passage in the conveyance direction; and
   a second inclined passage with downward inclination having an upper end at a position slightly spaced apart from an upper end of the first inclined passage in the conveyance direction, wherein
   the gap forming part includes a rod body which is provided with a plurality of projecting portions arranged in a staggered manner at predetermined intervals on a peripheral surface thereof, is arranged at the space formed between the upper ends in a state approximately orthogonal to the conveyance direction, and is rotatable about a center axis thereof, and
   the medicine packaging envelope strip is conveyed over the rod body while rotating the rod body thus forming a gap between the tablets by way of the projecting portion.

2. The tablet inspecting device according to claim 1, wherein the tablet inspecting device further comprises a flipping mechanism which flips one side portion of the medicine packaging envelope strip conveyed along the horizontal conveyance passage so as to scatter the tablets accommodated in a state where the tablets are densely collected on a side portion side within the medicine packaging envelope.

3. The tablet inspecting device according to claim 2, wherein the flipping mechanism includes:
   an elongated resilient member which extends downward on the side of the horizontal conveyance passage, wherein an upper end side of the elongated resilient member is supported and a lower end side of the elongated resilient member forms a free end at a position slightly away from the side of the horizontal conveyance passage; and
   a hammer portion which is rotated below the elongated resilient member and intermittently resiliently deforms a lower end side of the elongated resilient member in the direction approximately orthogonal to the conveyance direction and away from the medicine packaging envelope strip, wherein
   the elongated resilient member flips the side portion of the medicine packaging envelope strip when the elongated resilient member returns to an original state from an elastically deformed state.

4. The tablet inspecting device according to claim 1, wherein the tablet inspecting device further comprises an overlapping releasing part which includes a columnar or cylindrical rotary body which is arranged above the horizontal conveyance passage in a state where a center axis of the rotary body is approximately orthogonal to the conveyance direction and is rotatable about the center axis thereof, the overlapping releasing part being capable of releasing overlapping of the tablets which are accommodated in the medicine packaging envelope strip in a vertically overlapped state when the medicine packaging envelope strip passes a gap defined between the horizontal conveyance passage and the rotary body.

5. The tablet inspecting device according to claim 4, wherein the rotary body is elevatably provided.

6. The tablet inspecting device according to claim 1, wherein the gap forming part includes a biasing mechanism which constantly biases the rod body upward.

7. The tablet inspecting device according to claim 1, wherein the gap forming part includes an elevating/lowering mechanism which elevates and lowers the rod body.

8. The tablet inspecting device according to claim 1, wherein a guide plate having an approximately inverse-V-shape which guides a distal end of the medicine packaging envelope strip is provided at the space.

* * * * *